(12) United States Patent
Fotin-Mleczek et al.

(10) Patent No.: US 11,458,195 B2
(45) Date of Patent: *Oct. 4, 2022

(54) COMBINATION OF VACCINATION AND INHIBITION OF THE PD-1 PATHWAY

(71) Applicant: CureVac AG, Tübingen (DE)

(72) Inventors: Mariola Fotin-Mleczek, Sindelfingen (DE); Karl-Josef Kallen, Konigsdorf (DE); Jochen Probst, Wolfschlugen (DE)

(73) Assignee: CureVac AG, Tübingen (DE)

(*) Notice: Subject to any disclaimer, the term of this patent is extended or adjusted under 35 U.S.C. 154(b) by 460 days.

This patent is subject to a terminal disclaimer.

(21) Appl. No.: 16/555,586

(22) Filed: Aug. 29, 2019

(65) Prior Publication Data

US 2019/0381155 A1 Dec. 19, 2019

Related U.S. Application Data

(63) Continuation of application No. 15/890,736, filed on Feb. 7, 2018, now Pat. No. 10,434,158, which is a continuation of application No. 14/769,720, filed as application No. PCT/EP2014/000461 on Feb. 21, 2014, now Pat. No. 9,974,845.

(51) Int. Cl.
| | |
|---|---|
| *A61K 39/00* | (2006.01) |
| *A61K 39/395* | (2006.01) |
| *C07K 16/28* | (2006.01) |
| *A61P 35/00* | (2006.01) |
| *A61K 39/39* | (2006.01) |

(52) U.S. Cl.
CPC ...... *A61K 39/0011* (2013.01); *A61K 39/0005* (2013.01); *A61K 39/39* (2013.01); *A61K 39/3955* (2013.01); *A61K 39/39558* (2013.01); *C07K 16/2803* (2013.01); *C07K 16/2818* (2013.01); *A61K 2039/505* (2013.01); *A61K 2039/53* (2013.01); *A61K 2039/55516* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,008,449 B2 | 8/2011 | Korman et al. | |
| 8,168,757 B2 | 5/2012 | Finnefrock et al. | |
| 8,217,016 B2 | 7/2012 | Hoerr et al. | |
| 8,345,509 B2 | 1/2013 | Vu et al. | |
| 8,383,340 B2 | 2/2013 | Ketterer et al. | |
| 8,445,663 B2 | 5/2013 | Sällberg et al. | |
| 8,703,906 B2 | 4/2014 | Baumhof et al. | |
| 8,728,474 B2 | 5/2014 | Honjo et al. | |
| 8,968,746 B2 | 3/2015 | Baumhof et al. | |
| 9,155,788 B2 | 10/2015 | Hoerr et al. | |
| 9,974,845 B2 | 5/2018 | Fotin-Mleczek et al. | |
| 10,117,920 B2 | 11/2018 | Fotin-Mleczek et al. | |
| 10,307,472 B2 | 6/2019 | Fotin-Mleczek et al. | |
| 10,434,158 B2 | 10/2019 | Fotin-Mleczek et al. | |
| 2005/0032730 A1 | 2/2005 | Von Der Mülbe et al. | |
| 2005/0059624 A1 | 3/2005 | Hoerr et al. | |
| 2005/0250723 A1 | 11/2005 | Hoerr et al. | |
| 2006/0188490 A1 | 8/2006 | Hoerr et al. | |
| 2008/0025944 A1 | 1/2008 | Hoerr et al. | |
| 2008/0267873 A1 | 10/2008 | Hoerr et al. | |
| 2009/0324584 A1 | 12/2009 | Hoerr et al. | |
| 2010/0035973 A1 | 2/2010 | Walker | |
| 2010/0040614 A1 | 2/2010 | Ahmed et al. | |
| 2010/0048883 A1 | 2/2010 | Ketterer et al. | |
| 2010/0055102 A1 | 3/2010 | Solomon et al. | |
| 2010/0076060 A1 | 3/2010 | Sullenger et al. | |

(Continued)

FOREIGN PATENT DOCUMENTS

| | | |
|---|---|---|
| EP | 1392341 | 3/2005 |
| EP | 1604688 | 2/2010 |

(Continued)

OTHER PUBLICATIONS

Barber et al. "Restoring function in exhausted CDS T cells during chronic viral infection", *Nature*, 439:682-687, 2006.
Beck et al., 6th Annual European Antibody Congress 2010, *mAbs*, 3:2, 111-132, 2011.
Butte et al., "Programmed death-1 ligand 1 interacts specifically with the B7-1 costimulatory molecule to inhibit T cell responses", *Immunity*, 27:111-122, 2007.
Fleeton et al., "Self-Replicative RNA Vaccines Elicit Protection against Influenza A Virus, Respiratory Syncytial Virus, and a Tickborne Encephalitis Virus", *J. Infect. Dis.*, 183:1395-1398, 2001.
Gilboa, "The promise of cancer vaccines", *Nat. Rev. Cancer*, 4(5):401-411, 2004.
Ha et al., "Enhancing therapeutic vaccination by blocking PD-1-mediated inhibitory signals during chronic infection", *J. Exp. Med.*, 205(3):543-555, 2008.

(Continued)

*Primary Examiner* — Ilia I Ouspenski
(74) *Attorney, Agent, or Firm* — Parker Highlander PLLC

(57) ABSTRACT

The present invention relates to a vaccine/inhibitor combination comprising an RNA vaccine comprising at least one RNA comprising at least one open reading frame (ORF) coding for at least one antigen and a composition comprising at least one PD-1 pathway inhibitor, preferably directed against PD-1 receptor or its ligands PD-L1 and PD-L2. The present invention furthermore relates to a pharmaceutical composition and a kit of parts comprising the components of such a vaccine/inhibitor combination. Additionally the present invention relates to medical use of such a vaccine/inhibitor combination, the pharmaceutical composition and the kit of parts comprising such a vaccine/inhibitor combination, particularly for the prevention or treatment of tumor or cancer diseases or infectious diseases. Furthermore, the present invention relates to the use of an RNA vaccine in therapy in combination with a PD-1 pathway inhibitor and to the use of a PD-1 pathway inhibitor in therapy in combination with an RNA vaccine.

25 Claims, 3 Drawing Sheets

Specification includes a Sequence Listing.

(56) References Cited

U.S. PATENT DOCUMENTS

| | | |
|---|---|---|
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mülbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0053829 A1 | 3/2011 | Baumhof et al. |
| 2011/0077287 A1 | 3/2011 | Von Der Mülbe et al. |
| 2011/0250225 A1 | 10/2011 | Fotin-Mleczek et al. |
| 2011/0269950 A1 | 11/2011 | Von Der Mülbe et al. |
| 2011/0311472 A1 | 12/2011 | Hoerr et al. |
| 2012/0009221 A1 | 1/2012 | Hoerr et al. |
| 2012/0021043 A1 | 1/2012 | Kramps et al. |
| 2012/0141465 A1 | 6/2012 | Croft et al. |
| 2012/0213818 A1 | 8/2012 | Hoerr et al. |
| 2012/0258046 A1 | 10/2012 | Mutzke |
| 2013/0121988 A1 | 5/2013 | Hoerr et al. |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0209511 A1 | 8/2013 | Mebatsion et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0295043 A1 | 11/2013 | Kallen et al. |
| 2013/0295110 A1 | 11/2013 | Binder et al. |
| 2013/0336998 A1 | 12/2013 | Kallen et al. |
| 2014/0037660 A1 | 2/2014 | Fotin-Mleczek et al. |
| 2014/0086932 A1 | 3/2014 | Traber et al. |
| 2014/0294877 A1 | 10/2014 | Baumhof et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0086612 A1 | 3/2015 | Sahin et al. |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0206719 A1 | 7/2016 | Fotin-Mleczek et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0169201 A1 | 6/2018 | Fotin-Mleczek et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1* | 6/2019 | Fotin-Mleczek .. A61K 39/0011 |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1* | 11/2019 | Fotin-Mleczek ............... A61K 39/001194 |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1* | 3/2020 | Heidenreich ...... A61K 31/7105 |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2021/0198649 A1* | 7/2021 | Fotin-Mleczek ...... A61K 39/39 |

FOREIGN PATENT DOCUMENTS

| | | |
|---|---|---|
| EP | 2958588 | 8/2017 |
| EP | 3292873 | 3/2018 |
| WO | WO 1999/042585 | 8/1999 |
| WO | WO 2002/066044 | 8/2002 |
| WO | WO 2002/086063 | 10/2002 |
| WO | WO 2002/086083 | 10/2002 |
| WO | WO 2002/098443 | 12/2002 |
| WO | WO 2004/004743 | 1/2004 |
| WO | WO 2006/044923 | 4/2006 |
| WO | WO 2006/121810 | 11/2006 |
| WO | WO 2006/133396 | 12/2006 |
| WO | WO 2007/005874 | 1/2007 |
| WO | WO 2008/011344 | 1/2008 |
| WO | WO 2008/083174 | 7/2008 |
| WO | WO 2008/083949 | 7/2008 |
| WO | WO 2008/085562 | 7/2008 |
| WO | WO 2008/156712 | 12/2008 |
| WO | WO 2009/114335 | 9/2009 |
| WO | WO 2010/036959 | 4/2010 |
| WO | WO 2010/037408 | 4/2010 |
| WO | WO 2010/063011 | 6/2010 |
| WO | WO 2011/066389 | 6/2011 |
| WO | WO 2012/006369 | 7/2011 |
| WO | WO 2011/143656 | 11/2011 |
| WO | WO 2012/006634 | 1/2012 |
| WO | WO 2012/062218 | 5/2012 |
| WO | WO 2013/143555 | 10/2013 |
| WO | WO 2013/143683 | 10/2013 |
| WO | WO 2014/127917 | 8/2014 |
| WO | WO 2015/048312 | 4/2015 |
| WO | WO 2015/135558 | 9/2015 |
| WO | WO 2017/020026 | 2/2017 |
| WO | WO 2017/137095 | 8/2017 |
| WO | WO 2017/140905 | 8/2017 |
| WO | WO 2017/191258 | 11/2017 |
| WO | WO 2018/096179 | 5/2018 |
| WO | WO 2018/172556 | 9/2018 |

(56) References Cited

FOREIGN PATENT DOCUMENTS

| WO | WO 2018/211038 | 11/2018 |
|---|---|---|
| WO | WO 2019/038332 | 2/2019 |
| WO | WO 2019/077001 | 4/2019 |
| WO | WO 2019/092153 | 5/2019 |
| WO | WO 2019/122371 | 6/2019 |

OTHER PUBLICATIONS

Hung et al., "DNA vaccines for cervical cancer: from bench to bedside", *Exp. Mol. Med.*, 39(6):679-689, 2007.
Kreiter et al., "Tumor vaccination using messenger RNA: prospects of a future therapy", *Curr. Opin. Immunol.*, 23(3):399-406, 2011.
Li et al., "Potent Systemic Antitumor Immunity Induced by Vaccination with Chemotactic Prostate Tumor Associated Antigen Gene Modified Tumor Cell and Blockade of B7-H1", *J. Clin. Immunol.*, 27:117-130, 2007.
Monie et al., "Modification of Dendritic Cells to Enhance Cancer Vaccine Potency", Targeted Cancer Immune Therapy. Springer, New York, NY, pp. 133-157, 2009.
OMIM Entry 605402, creation date Nov. 14, 2000.
Pascolo, "Vaccination with Messenger RNA (mRNA)", Handbook Experimental Pharmacology 183:221-235, 2008.
Pilon-Thomas et al., "Blockade of programmed death ligand 1 enhances the therapeutic efficacy of combination immunotherapy against melanoma", *J. Immunol.*, 184:3442-3449, 2010.
Ribas, "Tumor immunotherapy directed at PD-1", *N. Engl. J. Med.*, 366(26):2517-2519, 2012.
Scheel et al., Final program for Society for Immunotherapy of Cancer (SITC) 26th annual meeting, pp. 54-55, Nov. 4-6, 2011.
Vogelzang and Agarwal, "Development of novel immune inteventions for genito-urinary cancers", In: Cancer Vaccines. Editors: Adrian Bot, Mihail Obrocea, Francesco M. marincola, CRC Press, pp. 25-43, 2011.
Agarwal and Vogelzang, "Development of novel immune inteventions for genito-urinary cancers." In: Cancer Vaccines. Editors: Adrian Bot, Mihail Obrocea, Francesco M. marincola, CRC Press, First published Aug. 23, 2011.
Berenbaum, "Synergy, additivism and antagonism in immunosuppression," *Clin. Exp. Immunol.* 28:1-18, 1977.
Brahmer et al., "Immune checkpoint inhibitors: making immunotherapy a reality for the treatment of lung cancer," *Cancer Immunol Res.* 1(2):85-91, 2013.
Clinical trial profile of the trial having ClinicalTrials.gov Identifier: NCT01176461, including the presentation of data as Abstract 8582; presented at the American Society of Clinical Oncology ASCO in 2012.
Clinical trial profile of the trial having ClinicalTrials.gov Identifier: NCT01176474, 2013.
Curran et al. "PD-1 and CTLA-4 combination blockade expands infiltrating T cells and reduces regulatory T and myeloid cells within B16 melanoma tumours," *PNAS*, 107(9):4275-4280, 2010.
Dai et al., "PD-1/PD-L1 blockade can enhance HIV-1 gag-specific T cell immunity elicited by dendritic cell-directed lentiviral vaccines," *Molecular Thrapy: The Journal of the American Society of Gene Therapy*, 20(9):1800-1809, 2012.
DrugBank Listing for Pembrolizumab, accessed on Jan. 18, 2018 at http://www.drugbank.ca/drugs/DB09037; 6 pages.
Duraiswamy et al., "Dual blockade of PD-1 and CTLA-4 combined with tumor vaccine effectively restores T cell rejection function in tumors," *Cancer Res.* 73(12):3591-603, 2013.
Fotin-Mleczek et al., "Highly potent mRNA based cancer vaccines represent an attractive platform for combination therapies supporting an improved therapeutic effect," *Journal of Gene Medicine*, 14(6):428-439, 2012.
Fotin-Mleczek et al., "Messenger RNA-based Vaccines With Dual Activity Induce Balanced TLR-7 Dependent Adaptive Immune Responses and Provide Antitumor Activity," *J. Immunother.* 34:1-15, 2011.

Hobo et al., "Improving dendritic cell vaccine immunogenicity by silencing PD-1 ligands using siRNA-lipid nanoparticles combined with antigen mRNA electroporation," *Cancer Immunol. Immunother.*, 62:285-297, 2013.
Hodi et al., "Improved Survival with Ipilimumab in Patients with Metastatic Melanoma," *N. Engl. J. Med.*, 363:711-723, 2010.
Hoerr, Abstract OP 57, "Stabilized Messenger RNA (RNActive™) as a Tool for Innovative Gene Delivery," presented at the BioStar 2006 2nd International Congress on Regenerative Biology and ICBN 2006 2nd International Congress on Bio-Nano-Interface held on Oct. 9 to 11, 2006, published in Tissue Engineering 13:886-887, Apr. 2007.
Iclozan and Gabrilovich. "Recent advances in immunotherapy of lung cancer," *J. Lung Cancer*, 11(1):428-439, 2012.
Li et al., "Anti-Programmed Death-1 Synergizes with Granulocyte Macrophage Colony-Stimulating Factor-Secreting Tumor Cell Immunotherapy Providing Therapeutic Benefit to Mice with Established Tumors," *Clin. Cancer Res.*, 15:1623-1634, 2009.
Lipson et al., "Durable cancer regression off-treatment and effective re-induction therapy with an anti-PD-1 antibody," *Clin. Cancer Res.*, 19(2):462-468, 2012.
Mackensen, "Peptide and RNA-based vaccines for the treatment of cancer," *Onkologie*, 34:202, 2011. Abstract V685 of the Jahrestagung der Deutschen, Österreichischen und Schweizerischen Gesellschaften für Hämatologie und Onkologie, Base, Sep. 30-Oct. 4, 2011.
Martinon et al., "Induction of virus-specific cytotoxic T lymphocytes in vivo by liposome-entrapped mRNA," *Eur. J. Immunol.* 23:1719-1722, 1993.
Melero et al. "Palettes of vaccines and 2009 immunostimulatory monoclonal antibodies for combination," *Clin. Cancer Res.*, 15(5):1507-1509, 2009.
Mkrtichyan et al., "Anti-PD-1 synergizes with cyclophosphamide to induce potent anti-tumor vaccine effects through novel mechanisms," *Eur. J. Immunol.* 41:2977-2986, 2011.
Monie et al., "Modification of Dendritic Cells to Enhance Cancer Vaccine Potency," *Targeted Cancer Immune Therapy*, Springer, New York, NY, 2009, 133-157.
Office Communication issued in corresponding U.S. Appl. No. 15/890,413, dated Apr. 11, 2018.
Office Communication issued in corresponding U.S. Appl. No. 14/769,720, dated Jun. 12, 2017.
Office Communication issued in corresponding U.S. Appl. No. 14/769,720, dated Sep. 14, 2017.
Office Communication issued in corresponding U.S. Appl. No. 14/769,720, dated Jan. 24, 2018.
OMIM Entry PD-1 *600244, 1994.
Omori et al. "Effects of interferon-a-transduced tumor cell vaccines and blockade of programmed cell death-1 on the growth of established tumors," *Cancer Gene Ther.* 19(9):637-643, 2012.
Pardoll, "The blockade of immune checkpoints in cancer immunotherapy," *Nat. Rev. Cancer*, 12:252-264, 2012.
Pascolo, "Vaccination with Messenger RNA, Methods in Molecular Medicine," 127:23-40, 2006.
PCT Search Report and Written Opinion issued in International Application No. PCT/US2014/000461, dated Jun. 5, 2014.
Postow et al., "Beyond cancer vaccines: a reason for future optimism with immunomodulatory therapy," *Cancer J.* 17(5):372-378, 2011.
Product Sheet Anti PD-1.
Rosenblatt et al. "CT-011, Anti-PD-1 Antibody, Enhances Ex-Vivo T Ceil Responses to Autologous Dendritic/Myeloma Fusion Vaccine Developed for the Treatment of Multiple Myeloma," *Blood*, 114:781, Abstract No. 781, 2009.
Rosenblatt et al., "PD-1 blockade by CT-011, anti-PD-1 antibody, enhances ex vivo T-cell responses to autologous dend ritic cell/ myeloma fusion vaccine," *J. Immunother.* 34:409-418, 2011.
Rossi et al., "Human dendritic cells: potent antigen-presenting cells at the crossroads of innate and adaptive immunity," *J. Immunol.* 175:1373-1381, 2005.
Schlake et al., "Developing mRNA-vaccine technologies" *RNA Biol.* 9(11):1319-1330, 2012.
Schurer et al., "A universal method to produce in vitro transcripts with homogeneous 3' ends", *Nucleic Acids Res.*, 30(12):56e-56, 2002.

(56) References Cited

OTHER PUBLICATIONS

Sierro et al., "Combination of lentivector immunization and low-dose chemotherapy or PD-1/PD-L1 blocking primes self-reactive T cells and induces anti-tumor immunity," *European Journal of Immunology*, 41(8):2217-2228, 2011.
Simes et al., Textual representation of the lecture of Stephen Simes, Biosante Pharmaceuticals Inc. at Jefferies Global Healthcare Conference, Jun. 6, 2012.
Slingluff, "The present and future of peptide vaccines for cancer: single or multiple, long or short, alone or in combination?" *Cancer J.*, 17(5):343-350, 2011.
Soares et al., "Granulocyte macrophage colony stimulating factor (GM-CSF) pancreas tumor vaccine in combination with blockade of PD-1 in a preclinical model of pancreatic cancer." In: Proceedings of the AACR Special Conference on Tumor Immunology: Multidisciplinary Science Driving Basic and Clinical Advances; Dec. 2-5, 2012; Miami, FL Philadelphia (PA): AACR; *Cancer Res.* 2013.
Song et al., "Enhancement of Vaccine-induced Primary and Memory CDS+ Tcell Responses by Soluble PD-1," *J. Immunother.*, 34:297-306, 2011.
Sriram et al., "Targeted cleavage of hepatitis E virus 3' end RNA mediated by hammerhead ribozymes inhibits viral RNA replication", *Virology*, 312(2):350-358, 2003.
Strain, "Crushing Cancer's Defenses: Vaccine approval offers hope while other armies muster," *Science News*, 179(10):20-23, 2011.
Topalian et al., "Safety, Activity, and Immune Correlates of Anti-PD-1 Antibody in Cancer," *N. Engl. J. Med.*, 366(26):2443-2254.
Ulmer et al., "RNA-based vaccines," *Vaccine*, 30(30):4414-4418, 2012.
Vanham and Van Gulck, "Can immunotherapy be useful as a 'functional cure' for infection with Human Immunodeficiency Virus-1?" *Retrovirology*, 9(1):72, 2012.
Weber, "Immune checkpoint proteins: a new therapeutic paradigm for cancer—preclinical background: CTLA-4 and PD-1 blockade" *Semin. Oncol.*, 37(5):430-439, 2010.
Weide et al., "Plasmid DNA-and messenger RNA-based anti-cancer vaccination," *Immunol. Lett.*, 115 (1), 33-42, 2008.
Wong et al., "Programmed death-1, blockade enhances expansion and functional capacity of human melanoma antigen-specific CTLs," *International immunology* 19(10):1223-1234, 2007.
Yao et al., "Advances in targeting cell surface signalling molecules for immune modulation," *Nat. Rev. Drug Discov.*, 12(2):130, 2013.
Zhou et al., "Blockade of Programmed Death-I Pathway Rescues the Effector Function of Tumor-Infiltrating T Cells and Enhances the Antitumor Efficacy of Lentivector Immunization," *J. Immunol.* 185:5082-5092, 2010.
Zitvogel et al., "Targeting PD-1/PD-L1 interactions for cancer immunotherapy," *Oncoimmunology*, 1(8):1223-1225, 2012.
Dollins et al., "Assembling OX40 aptamers on a molecular scaffold to create a receptor-activating aptamer", *Chem. Biol.*, 15:675-682, 2008.
Editorial Policies of the American Association for Cancer Research.
Evans et al., "Engagement of OX40 enhances antigen-specific CD4+ T cell mobilization/memory development and humoral immunity: comparison of αOX-40 with αCTLA-4", *J. Immuno.*, 167:6804-6811, 2001.
International Search Report issued in corresponding PCT Application No. PCT/EP2014/000659, dated Jul. 11, 2014.
Jensen et al., "Signaling through OX40 enhances antitumor immunity", *Semin. Oncol.*, 37:524-532, 2010.
Liu et al., "The adjuvancy of OX40 ligand (CD252) on an HIV-1 canarypox vaccine", *Vaccine*, 27(37): 5077-5084, 2009.
Melero et al., "Agonist antibodies to TNFR molecules that costimulate T and NK cells", *Clin. Cancer Res.*, 19:1044-1053, 2013.
Murata et al., "OX40 Costimulation Synergizes with GM-CSF Whole-Cell Vaccination to Overcome Established CD8+ TCell Tolerance to an Endogenous Tumor Antigen", *J. Immunology*, 176(2): 974-983, 2006.
Notice of Opposition issued in corresponding European Patent No. 3116535, submitted on May 7, 2020.

Qian et al., "Active Vaccination with Dickkopf-1 induces protective and therapeutic antitumor immunity in murine multiple myeloma", *Blood*, 119:161-169, 2012.
Redmond et al., "Defects in the acquisition of CD8 T cell effector function after priming with tumor or soluble antigen can be overcome by the addition of an OX40 agonist", *J. Immunol.*, 179:7244-7253, 2007.
Salek-Ardakani et al., "Targeting OX40 promotes lung-resident memory CD8 T cell populations that protect against respiratory poxvirus infection", *J. Virol.*, 85:9051-9059, 2011.
Vezys et al., "4-1BB signaling synergizes with programmed death ligand 1 blockade to augment CD8 T cell responses during chronic viral infection", *J. Immunol.*, 187:1634-1642, 2011.
Weinberg et al., "Anti-OX40 (CD134) Administration to Nonhuman Primates: Immunostimulatory Effects and Toxicokinetic Study", *J. Immunother.*, 29:575-585, 2006.
Blank et al. "Blockade of PD-L1 (B7-H1) augments human tumor-specific T cell responses in vitro," *Int. J. Cancer*, 119:317-327, 2006.
Brahmer et al. "Safety and Activity of Anti-PD-L1 Antibody in Patients with Advanced Cancer," *N. Engl. J. Med.*, 366(26): 2455-2465, 2012.
Burova et al., "Combined treatment with anti-LAG-3 and anti-PD-1 fully human monoclonal antibodies inhibits tumor growth in immunocompetent double humanized LAG-3/PD-1 mice," *Cancer Research*, 76(Suppl 14):1484, 2016.
Experimental Details OVA Experiments filed in Opposition of EP 3292873 Proprietor Response dated Aug. 28, 2020.
Experimental Details Pentatope Experiments filed in Opposition of EP 3292873 Proprietor Response dated Aug. 28, 2020.
Foy et al., "Poxvirus-Based Active Immunotherapy with PD-1 and LAG-3 Dual Immune Checkpoint Inhibition Overcomes Compensatory Immune Regulation, Yielding Complete Tumor Regression in Mice," PLoS One, e0150084, 2016.
Goding et al., "Combination of adoptive cell transfer, anti-PD-L1 and anti-LAG-3 antibodies for the treatment of recurrent tumors better with more," *Oncoimmunology*, 2(8):1-3, 2013.
Grunwitz et al., "HPV16 RNA-LPX vaccine mediates complete regression of aggressively growing HPV-positive mouse tumors and establishes protective T cell memory," *Oncoimmunol.*, 8(9):e1629259, 2019.
Huang et al., "LAG3 and PD1 co-inhibitory molecules collaborate to limit CD8+ T cell signaling and dampen antitumor immunity in a murine ovarian cancer model," Oncotarget, 6:27359-27377, 2015.
La Motte-Mohs et al., American Association for Cancer Research Annual Meeting, poster 3217, 2016.
Lote et al., "PD-1 and PD-L1 blockade in gastrointestinal malignancies," Cancer Treatment Reviews, 41:893-903, 2015.
Mahoney et al., "Combination cancer immunotherapy and new immunomodulatory targets," *Nature Rev.*, 14:561-584, 2015.
Matsuzaki et al., "Tumor-infiltrating NY-ESO-1-specific CD8+ T cells are negatively regulated by LAG-3 and PD-1 in human ovarian cancer," PNAS, 107:7875-7880, 2010.
NCI Drug Dictionary, Durvalumab, collected May 27, 2018.
Office Communication issued in U.S. Appl. No. 16/494,422, dated Jul. 24, 2020.
Office Communication issued in U.S. Appl. No. 16/494,422, dated Feb. 5, 2021.
Office Communication issued in U.S. Appl. No. 16/494,422, dated Sep. 10, 2021.
Office Communication issued in U.S. Appl. No. 16/494,422, dated Mar. 23, 2022.
Opposition of EP 3292873, Notice from BioNTech dated, Jan. 31, 2020.
Opposition of EP 3292873, Notice from eTheRNA dated, Feb. 3, 2020.
Opposition of EP 3292873, Notice from James Poole, dated Feb. 3, 2020.
Opposition of EP 3292873, Notice from Merck, dated Jan. 31, 2020.
Opposition of EP 3292873, Notice from Pfizer, dated Feb. 3, 2020.
Opposition of EP 3292873, Notice from Stawman, dated Jan. 31, 2020.

(56) References Cited

OTHER PUBLICATIONS

Opposition of EP 3292873, Proprietor Response, dated Aug. 28, 2020.
PCT International Search Report and Written Opinion issued in International Application No. PCT/EP2018/056774, dated Apr. 13, 2018.
Sharma and Allison, "The future of immune checkpoint therapy," *Science*, 348(6230):56-61, 2015.
Topalian et al., "Targeting the PD-1/B7-H1(PD-L1) pathway to activate anti-tumor immunity," *Current Opin. Immunol.*, 24:207-212, 2012.
Verbeke et al., "Broadening the Message: A Nanovaccine Co-loaded with Messenger RNA and α-GalCer Induces Antitumor Immunity through Conventional and Natural Killer T Cells," *ACS Nano*, 13:1655-1669, 2019.
Wang et al., "mRNA Vaccine with Antigen-Specific Checkpoint Blockade Induces an Enhanced Immune Response against Established Melanoma," *Mol. Ther.* 26(2):1-15, 2018.
Woo et al., "Immune inhibitory molecules LAG-3 and PD-1 synergistically regulate T-cell function to promote tumoral immune escape," Cancer Research, 72:917-927, 2012.

\* cited by examiner

R1710:
GGGAGAAAGCUUACCAUGGGCAGCAUCGGGGCCGCGUCGAUGGAGUUCUGCU
UCGACGUGUUCAAGGAGCUGAAGGUCCACCACGCCAACGAGAACAUCUUCUA
CUGCCCGAUCGCCAUCAUGAGCGCGCUCGCCAUGGUGUACCUGGGCGCCAAG
GACAGCACCCGGACGCAGAUCAACAAGGUGGUCCGCUUCGACAAGCUGCCCG
GCUUCGGGGACUCGAUCGAGGCGCAGUGCGGCACCAGCGUGAACGUGCACAG
CUCGCUCCGGGACAUCCUGAACCAGAUCACCAAGCCGAAC
GACGUCUACAGCUUCAGCCUGGCCUCGCGGCUCUACGCCGAGGAGCGCUACC
CGAUCCUGCCCGAGUACCUGCAGUGCGUGAAGGAGCUCUACCGGGGCGGGCU
GGAGCCGAUCAACUUCCAGACGGCGGCCGACCAGGCCCGGGAGCUGAUCAAC
AGCUGGGUGGAGAGCCAGACCAACGGCAUCAUCCGCAACGUCCUCCAGCCGU
CGAGCGUGGACAGCCAGACCGCGAUGGUGCUGGUCAACGCCAUCGUGUUCAA
GGGCCUGUGGGAGAAGACGUUCAAGGACGAGGACACCCAG
GCCAUGCCCUUCCGGGUGACCGAGCAGGAGUCGAAGCCGGUCCAGAUGAUGU
ACCAGAUCGGGCUCUUCCGGGUGGCGAGCAUGGCCAGCGAGAAGAUGAAGAU
CCUGGAGCUGCCGUUCGCCUCGGGCACGAUGAGCAUGCUCGUGCUGCUGCCC
GACGAGGUCAGCGGCCUCGAGCAGCUGGAGUCGAUCAUCAACUUCGAGAAGC
UGACCGAGUGGACCAGCAGCAACGUGAUGGAGGAGCGCAAGAUCAAGGUGUA
CCUCCCGCGGAUGAAGAUGGAGGAGAAGUACAACCUGACG
UCGGUCCUGAUGGCGAUGGGGAUCACCGACGUGUUCAGCAGCUCGGCCAACC
UCAGCGGCAUCAGCUCGGCCGAGAGCCUGAAGAUCAGCCAGGCGGUGCACGC
CGCCCACGCGGAGAUCAACGAGGCCGGCCGGGAGGUCGUGGGGUCGGCCGAG
GCGGGCGUGGACGCCGCCAGCGUCAGCGAGGAGUUCCGCGCGGACCACCCGU
UCCUGUUCUGCAUCAAGCACAUCGCCACCAACGCCGUGCUCUUCUUCGGCCG
GUGCGUGUCGCCCUGACCACUAGUUAUAAGACUGACUAGC
CCGAUGGGCCUCCCAACGGGCCCUCCUCCCCUCCUUGCACCGAGAUUAAUAA
AAAAAAAAAAAAAAAAAAAAAAAAAAAAAAAAAAAAAAAAAAAAAAAAAAAA
AAAAAAAAAAUGCAUCCCCCCCCCCCCCCCCCCCCCCCCCCCCCCAAAGGC
UCUUUUCAGAGCCACCAGAAUU

Fig. 3

COMBINATION OF VACCINATION AND INHIBITION OF THE PD-1 PATHWAY

This application is a continuation of U.S. application Ser. No. 15/890,736, filed Feb. 7, 2018, which is a continuation of U.S. application Ser. No. 14/769,720, filed Aug. 21, 2015, now U.S. Pat. No. 9,974,845, which is a national phase application under 35 U.S.C. § 371 of International Application No. PCT/EP2014/000461, filed Feb. 21, 2014, which claims priority to International Application No. PCT/EP2013/000526, filed Feb. 22, 2013. The entire text of each of the above referenced disclosures is specifically incorporated herein by reference.

The sequence listing that is contained in the file named "CRVCP0138USC4.txt", which is 6 KB (as measured in Microsoft Windows®) and was created on Aug. 28, 2019, is filed herewith by electronic submission and is incorporated by reference herein.

The present invention relates to a vaccine/inhibitor combination comprising an RNA vaccine comprising at least one RNA comprising at least one open reading frame (ORF) coding for at least one antigen and a composition comprising at least one PD-1 pathway inhibitor, preferably directed against PD-1 receptor or its ligands PD-L1 and/or PD-L2. The present invention furthermore relates to a pharmaceutical composition and a kit of parts comprising such a vaccine/inhibitor combination. Additionally, the present invention relates to the medical use of such a vaccine/inhibitor combination, the pharmaceutical composition and the kit of parts comprising such a vaccine/inhibitor combination, particularly for the prevention or treatment of tumor or cancer diseases or infectious diseases. Furthermore, the present invention relates to the use of an RNA vaccine in therapy in combination with a PD-1 pathway inhibitor and to the use of a PD-1 pathway inhibitor in therapy in combination with an RNA vaccine.

Traditionally, cancer immunotherapy was focused on stimulating the immune system through vaccination or adoptive cellular immunotherapy to elicit an anti-tumor response. This approach was based on the assumption that tumor cells express antigenic targets but that anti-tumor T cells were not sufficiently activated. Therefore, to circumvent this problem, it was mainly tried to increase the recognition of these antigenic targets by stimulating key positive co-stimulatory and innate immune pathways (such as CD28, CD154 and TLR receptors).

More recently, it became clear that the immune system does recognize tumor antigens but remains quiescent although tumor antigens are present. This observation led to the hypothesis that there are specific inhibitory mechanisms which limit or even shut down the anti-tumor response. This hypothesis was confirmed when negative regulatory T cell surface molecules were discovered which are upregulated in activated T cells to dampen their activity, resulting in less effective killing of tumor cells. These inhibitory molecules were termed negative co-stimulatory molecules due to their homology to the T cell co-stimulatory molecule CD28. These proteins, also referred to as immune checkpoint proteins, function in multiple pathways including the attenuation of early activation signals, competition for positive co-stimulation and direct inhibition of antigen presenting cells (B our-Jordan et al., 2011. Immunol Rev. 241(1):180-205; PMID: 21488898). One member of this protein family is programmed death-1 (PD-1) and its ligands B7-H1/PD-L1 (CD274) and B7-DC/PD-L2 (CD273).

PD-1 is expressed on activated T and B cells as well as on monocytes involved in regulating the balance between immune activation and tolerance. The major role of PD-1 is to limit the activity of T cells in the periphery during an inflammatory response to infection and to limit autoimmunity. The basis for this regulation is that the PD-1 ligands B7-H1/PD-L1 and B7-DC/PD-L2 are upregulated in response to various proinflammatory cytokines and can bind to PD-1 on activated T cells in inflamed tissues, thereby limiting the immune response. Deletion of the PD-1 gene leads to autoimmune complications, for example lupus-like symptoms (Nishimura et al., 1999. Immunity 11(2):141-51; PMID: 10485649).

In addition, it was found that B7-H1/PD-L1 is frequently upregulated on many different tumor types, where it inhibits local anti-tumor T cell responses by binding to PD-1 on tumor infiltrating lymphocytes. For example, it was demonstrated that PD-L1 plays a role in tumor immune evasion in squamous cell carcinomas of the head and neck (Dong et al., 2002. Nat Med. 8(8):793-800). The authors showed that forced expression of B7-H1/PD-L1 in tumors that are normally B7-H1/PD-L1 negative inhibits their immune elimination and that antibody blockade restores anti-tumor responses. Furthermore, it was shown that many human tumors, such as carcinomas of the lung, ovary and colon, upregulate B7-H1/PD-L1 relative to their normal tissue counterparts. In summary, these observations suggested to use blockade of the PD-1 pathway for cancer immunotherapy (Zitvogel and Kroemer, 2012. Oncoimmunology 1, 1223-1125).

In this context US2010/0055102 describes the use of PD-1 antagonists for increasing a T cell immune response in a mammal.

Recently, the first clinical trials with immune checkpoint inhibitors (ICIs) against the PD-1 receptor and its ligand PD-L1 have been reported. The first phase I trial with the anti-PD-1 monoclonal antibody BMS-936558 was conducted in patients with treatment-refractory metastatic solid tumors. Clinical activity was observed in patients with melanoma, renal carcinoma, colorectal cancer and non-small cell lung cancer (NSCLC). It could be shown that PD-L1 is overexpressed in many cancers and is often associated with poor prognosis. Furthermore tumor cell surface expression of PD-L1 in pretreatment biopsies emerged as a potential biomarker of response, consistent with pathway biology (Brahmer et al., 2010. J Clin Oncol. 28(19):3167-75; PMID: 20516446).

Another clinical study with BMS-936558 produced objective responses in approximately one in four to one in five patients with non-small-cell lung cancer, melanoma, or renal-cell cancer; the adverse-event profile does not appear to preclude its use. Preliminary data suggest a relationship between PD-L1 expression on tumor cells and objective response (Topalian et al., 2012. N Engl J Med. 366(26):2443-54; PMID: 22658127).

Furthermore, a phase I study with the anti-PD-L1 antibody BMS-936559 induced durable tumor regression (objective response rate of 6 to 17%) and prolonged stabilization of disease (rates of 12 to 41% at 24 weeks) in patients with advanced cancers, including non-small-cell lung cancer, melanoma, and renal-cell cancer. Specifically, an objective response (a complete or partial response) was observed in 9 of 52 patients with melanoma, 2 of 17 with renal-cell cancer, 5 of 49 with non-small-cell lung cancer, and 1 of 17 with ovarian cancer (Brahmer et al. 2012. N Engl J Med. 366(26):2455-65; PMID: 22658128).

Nevertheless, only relatively low responses of some cancers could be demonstrated in these studies (e.g. lung and prostate cancer) to PD-1 pathway checkpoint inhibitors. In more recent studies combinations with PD-1 pathway checkpoint inhibitors have been evaluated in preclinical models.

A study reported e.g. the generation of a dendritic cell (DC) vaccine with a combination of a PD-1 ligand siRNA and target antigen mRNA. These PD-L1-silenced DC's loaded with antigen mRNA increased ex vivo antigen-specific CD8+ T cell responses from transplanted cancer patients (Hobo et al. 2013. Cancer Immunol Immunother. 62(2):285-97; PMID: 22903385)

Likewise, Dai et al. showed that a dendritic cell-directed lentiviral vector (DCLV) system encoding the human immunodeficiency virus (HIV)-1 Gag protein combined with blocking of the PD-1/PD-1 ligand (PD-L) inhibitory signal via an anti-PD-L1 antibody generated an enhanced HIV-1 Gag-specific CD8+ immune response following DCLV immunization (Dai et al. 2012. Mol Ther. 20(9):1800-9; PMID: 22588271).

Another study examined the combination of recombinant lentivector (rLV) vaccination with PD-1 and PD-L1 blocking antibodies. Combining blocking antibodies with rLV vaccination delayed tumor growth but was not sufficient to induce the complete rejection of established tumors (Sierro et al. 2011. Eur J Immunol.; 41(8):2217-28; PMID: 21538347).

Additionally, WO2008/11344 discloses the modulation of an immune response by combination of a DNA-based recombinant adenoviral construct (rAAV) coding for an antigen or therapeutic protein and a nucleic acid coding for a modulator of PD-1 signaling, particularly siRNA, anti-sense RNA or a ribozyme specific for PD-L1 gene.

In this context also the fusion of soluble PD-1 protein and antigenic protein fragments was studied (WO2012/062218).

A further preclinical study reported that combination blockade of the CTLA-4- and PD-1-negative costimulatory receptors leads to synergistic levels of tumor rejection in the context of a suitable vaccine (Curran et al., 2010. Proc Natl Acad Sci USA 107(9):4275-80; PMID: 20160101). Mice preimplanted with B16 melanoma cells were vaccinated with irradiated B16 melanoma cells expressing either GM-CSF (Gvax) or Flt3-ligand (Fvax) combined with antibody blockade of the negative T-cell costimulatory receptor cytotoxic T-lymphocyte antigen-4 (CTLA-4), programmed death-1 (PD-1) and its ligand PD-L1. In the context of Gvax, neither blockade of any single co-inhibitory receptor nor of any combination resulted in greater than 20% survival. Using Fvax, blockade of either PD-L1 (8% survival), CTLA-4 (10% survival), or PD-1 (25% survival) showed modest therapeutic benefit. However, only combined blockade of CTLA-4 and PD-1 led to tumor rejection in 50% of mice and further addition of anti-PD-L1 antibody increased the rate to 65%. In summary, only CTLA-4-blockade combined with PD-1 blockade had a significant effect in promoting the rejection of B16 melanomas in conjunction with the B16 melanoma cell vaccine. Blocking of a single inhibitory receptor (PD-1 or CTLA-4) leads to upregulation of the unblocked pathway. Therefore, this study suggests that a simultaneous blockade of multiple negative co-stimulatory receptors may be required to enable tumor-infiltrating T cells to be effective. Furthermore, based on their preclinical data in the B16 melanoma model, the authors suggest that combining these agents may have synergistic effects in driving tumor rejection but they remark that combining multiple co-inhibitory blocking antibodies in the clinic should proceed with great caution.

Mkrtichya et al. additionally reported synergistic antigen-specific immune responses by using an anti-PD-1 antibody (CT-011) with Treg-cell depletion by low-dose cyclophosphamide (CPM), combined with a tumor vaccine (HPV16-E7 peptide vaccine). But only the combination of these 3 treatments resulted in a complete regression of tumors (Mkrtichya et al. 2011. Eur J Immunol. 41(10):2977-86; PMID: 21710477)

A further report examining the effect of PD-L1 inhibition on tumor growth showed that the systemic administration of anti-PD-L1 antibody plus melanoma peptide-pulsed dendritic cells (DCs) resulted in a higher number of melanoma peptide-specific CD8+ T cells, but that this combination was insufficient to delay the growth of established B16 melanoma. Although the additional body irradiation delayed tumor growth, further adoptive transfer of antigen-specific CD8+ T cells was needed to achieve tumor regression and long-term survival of the treated mice (Pilon-Thomas et al. 2010. J Immunol. 1; 184(7):3442-9; PMID: 20194714).

In a preclinical study Fotin-Mleczek et al. showed the beneficial combination of a tumour vaccine based on mRNA and an antibody directed against the CTLA4 receptor which attenuates the signaling of T cells (Fotin-Mleczek et al., 2012. J Gene Med. 14(6):428-39; PMID: 22262664).

In summary, the use of immune checkpoint inhibitors appears to represent a promising approach for improved cancer immunotherapy. However, the combination of vaccines with a single ICI often did not lead to the hoped improvement of the immunotherapy and the combined clinical use of ICIs targeting multiple negative co-stimulatory receptors or the combination of ICIs with other treatments may induce clinical complications as e.g. induction of an autoimmune disease.

Therefore, it is the object of the present invention to provide safe and effective means for a therapy based on ICIs, particularly based on PD-1 pathway inhibitors, in particular for a therapy of tumor, cancer and/or infectious diseases.

The object underlying the present invention is solved by the claimed subject matter. In particular, the object of the invention is solved by the provision of a vaccine/inhibitor combination comprising as vaccine an RNA vaccine comprising at least one RNA comprising at least one open reading frame coding for at least one antigen and as inhibitor a PD-1 pathway inhibitor, preferably directed against PD-1 receptor or its ligands PD-L1 and/or PD-L2. Furthermore, the object is solved by a pharmaceutical composition or a kit of parts comprising the vaccine/inhibitor combination or the respective components thereof. Additionally, the object is solved by a combination of an RNA vaccine with ICIs, particularly PD-1 pathway inhibitors for use in a method of treatment of tumour or cancer diseases or infection diseases.

For the sake of clarity and readability the following definitions are provided. Any technical feature mentioned for these definitions may be read on each and every embodiment of the invention. Additional definitions and explanations may be specifically provided in the context of these embodiments.

Immune response: An immune response may typically either be a specific reaction of the adaptive immune system to a particular antigen (so called specific or adaptive immune response) or an unspecific reaction of the innate immune system (so called unspecific or innate immune response). In essence, the invention is associated with specific reactions (adaptive immune responses) of the adaptive immune system. However, this specific response can be supported by an additional unspecific reaction (innate immune response). Therefore, the invention also relates to a compound, composition or combination for simultaneous stimulation of the innate and the adaptive immune system to evoke an efficient adaptive immune response.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

Humoral immunity/humoral immune response: Humoral immunity refers typically to antibody production and optionally to accessory processes accompanying antibody production. An humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The vaccine/inhibitor combination, the pharmaceutical composition or the kit of parts according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which comprises at least one epitope and which may be presented by the MHC to T cells. In the sense of the present invention an antigen may be the product of translation of a provided RNA, preferably an mRNA as defined herein. In this context, also fragments, variants and derivatives of peptides and proteins comprising at least one epitope are understood as antigens. In the context of the present invention, tumour antigens and pathogenic antigens as defined herein are particularly preferred.

Epitope: Epitopes (also called 'antigen determinant') can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Vaccine: A vaccine is typically understood to be a prophylactic or therapeutic material providing at least one antigen, preferably an immunogen. "Providing at least on antigen" means, for example, that the vaccine comprises the antigen or that the vaccine comprises a molecule that, e.g., codes for the antigen or a molecule comprising the antigen. For example, the vaccine may comprise a nucleic acid, such as an RNA (e.g. RNA vaccine), which codes for a peptide or protein that comprises the antigen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In the context, of the present invention, the vaccine preferably does not comprise cells, such as dendritic cells or cancer cells, e.g., B16 melanoma cells. Furthermore, in the context of the present invention the vaccine preferably does not consist of peptide antigens, such as peptide tumor antigens. In the context of the present invention, the vaccine is preferably an RNA vaccine.

RNA vaccine: An RNA vaccine is defined herein as a vaccine comprising at least one RNA molecule comprising at least one open reading frame (ORF) coding for at least one antigen. In the context of the present invention, the at least one RNA molecule comprised by the vaccine is preferably an isolated RNA molecule. This at least one RNA is preferably viral RNA, self-replicating RNA (replicon) or most preferably mRNA. Also included herein are RNA/DNA hybrids which means that the at least one RNA molecule of the RNA vaccine consists partially of ribonucleotides and partially of deoxyribonucleotides. In this context, the at least one RNA of the RNA vaccine consists to at least 50% of ribonucleotides, more preferably to at least 60%, 70%, 80%, 90% and most preferably to 100%. In this context, the at least one RNA of the RNA vaccine can also be provided as complexed RNA or mRNA, as virus particle and as replicon particle as defined herein. In the context of the present invention, the at least one RNA comprised by the RNA vaccine is preferably not present in cells, such as in dendritic cell or cancer cells, e.g. B16 melanoma cells. Furthermore it is particularly preferred that the RNA vaccine of the invention does not comprise or does not consist of a lentiviral vector, in particular not a dendritic cell—directed lentiviral vector, or an (recombinant) adenoviral/adeno-associated vector ((r)AAV vector). Preferably, the RNA vaccine of the invention is not an HIV vaccine. In particular, it is preferred that the RNA vaccine of the invention does not comprise an AAV or lentiviral vector encoding one or more antigens. Also, the RNA vaccine of the invention may preferably not encode HIV-specific antigens, e.g. Gag protein, in particular not a lentiviral vector encoding HIV specific antigens, like Gag. Preferably, the RNA vaccine of the invention does not comprise a fusion protein of a PD1 protein and an antigenic protein or a fusion protein of a PD1 protein and an immunoglobulin or a portion thereof and does not encode such a PD1 fusion protein.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an (isolated) RNA as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Nucleic acid: The term nucleic acid means any DNA- or RNA-molecule and is used synonymous with polynucleotide. Furthermore, modifications or derivatives of the nucleic acid as defined herein are explicitly included in the general term "nucleic acid". For example, PNA is also included in the term "nucleic acid".

Monocistronic RNA: A monocistronic RNA may typically be an RNA, preferably an mRNA, that comprises only one open reading frame. An open reading frame in this context is a sequence of several nucleotide triplets (codons) that can be translated into a peptide or protein.

Bi-/multicistronic RNA: RNA, preferably mRNA, that typically may have two (bicistronic) or more (multicistronic) open reading frames (ORF). An open reading frame in this context is a sequence of several nucleotide triplets (codons) that can be translated into a peptide or protein.

5'-Cap structure: A 5' Cap is typically a modified nucleotide, particularly a guanine nucleotide, added to the 5' end of an RNA molecule. Preferably, the 5'-Cap is added using a 5'-5'-triphosphate linkage.

Poly(C) sequence: A poly(C) sequence is typically a long sequence of cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid.

Poly(A) tail: A poly(A) tail also called "3'-poly(A) tail" is typically a long sequence of adenine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a nucleic acid sequence, preferably an mRNA. A poly(A) tail may preferably be located 3' of the coding region comprised by a nucleic acid, e.g. an mRNA.

Stabilized nucleic acid: A stabilized nucleic acid, typically, may be essentially resistant to in vivo degradation (e.g. degradation by an exo- or endo-nuclease) and/or ex vivo degradation (e.g. by the manufacturing process prior to vaccine administration, e.g. in the course of the preparation of the RNA vaccine solution to be administered). Stabilization of RNA, particularly mRNA can, e.g., be achieved by providing a 5'-Cap structure, a Poly(A) tail, a poly (C) tail, and/or any other UTR modification. It can also be achieved by backbone modification, sugar modification, base modification, and/or modification of the G/C-content of the nucleic acid. Various other methods are conceivable in the context of the invention.

Modification of a nucleic acid (modified nucleic acid): Modification of a nucleic acid molecule, particularly of RNA or mRNA, may contain backbone modifications, sugar modifications or base modifications. A backbone modification in connection with the present invention is a modification in which phosphates of the backbone of the nucleotides contained in the nucleic acid molecule are chemically modified. A sugar modification in connection with the present invention is a chemical modification of the sugar of the nucleotides of the nucleic acid. Furthermore, a base modification in connection with the present invention is a chemical modification of the base moiety of the nucleotides of the nucleic acid molecule. Therefore a modified nucleic acid is also defined herein as a nucleic acid molecule which may include nucleotide analogues. Furthermore a modification of a nucleic acid molecule can contain a lipid modification. Such a lipid-modified nucleic acid typically comprises a nucleic acid as defined herein. Such a lipid-modified nucleic acid molecule typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule.

A modification of a nucleic acid may also comprise the modification of the G/C content of the coding region of a nucleic acid molecule, especially of the at least one RNA of the RNA vaccine encoding at least one antigen in the inventive vaccine/inhibitor combination. In this context it is particularly preferred that the G/C content of the coding region of the nucleic acid molecule is increased, compared to the G/C content of the coding region of its particular wild type coding sequence, i.e. the unmodified RNA. The encoded amino acid sequence of the nucleic acid sequence is preferably not modified compared to the coded amino acid sequence of the particular wild type mRNA. The modification of the G/C-content of the nucleic acid molecule, especially if the nucleic acid molecule is in the form of an mRNA or codes for an mRNA, is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. Therefore, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Preferably, the G/C content of the coding region of the nucleic acid molecule, especially of the at least one RNA of the RNA vaccine encoding at least one antigen in the inventive vaccine/inhibitor combination, is increased by at least 7%, more preferably by at least 15%, particularly preferably by at least 20%, compared to the G/C content of the coded region of the wild type mRNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment, variant and/or derivative thereof or the whole sequence of the wild type mRNA sequence or coding sequence are substituted, thereby increasing the G/C content of said sequence. In this context, it is particularly preferable to increase the G/C content of the nucleic acid molecule, especially of the at least one RNA of the RNA vaccine encoding at least one antigen in the inventive vaccine/inhibitor combination, to the maximum (i.e. 100% of the substitutable codons), in particular in the region coding for a protein, compared to the wild type sequence. Furthermore a modification of the nucleic acid, especially of the at least one RNA of the RNA vaccine encoding at least one antigen in the inventive vaccine/inhibitor combination, is based on the finding that the translation efficiency is also determined by a different frequency in the occurrence of tRNAs in cells. The frequency in the occurrence of tRNAs in a cell, and thus the codon usage in said cell, is dependent on the species the cell is derived from. Accordingly, a yeast cell generally exhibits a different codon usage than a mammalian cell, such as a human cell. Thus, if so-called "rare codons" are present in the nucleic acid molecule (with respect to the respective expression system), especially if the nucleic acid is in the form of an mRNA or codes for an mRNA, to an increased extent, the corresponding modified nucleic acid molecule is translated to a significantly poorer degree than in the case where codons coding for relatively "frequent" tRNAs are present. Therefore, the coding region of the modified nucleic acid, particularly the at least one RNA of the RNA vaccine encoding at least one antigen in the inventive vaccine/inhibitor combination is preferably modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid molecule, particularly of the at least one RNA of the RNA vaccine encoding at least one antigen in the inventive vaccine/inhibitor combination, is modified such that codons for which frequently occurring tRNAs are available are inserted. In other words, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA. Such a modified nucleic acid, preferably is termed herein as "codon-optimized nucleic acid or RNA". Which tRNAs occur relatively frequently in the cell and which, in contrast, occur relatively rarely is known to a person skilled in the art; cf. e.g. Akashi, Curr. Opin. Genet. Dev. 2001, 11(6): 660-666. It is particularly preferred that a nucleic acid sequence coding for a protein, particularly the at least one RNA coding for at least one antigen comprised by the RNA vaccine, used in the present invention is codon optimized for the human codon usage. The codons which use for the particular amino acid the tRNA which occurs the most frequently, e.g. the Gly codon, which uses the tRNA which occurs the most frequently in the (human) cell, are particularly preferred. In this context, it is particularly preferable to link the sequential G/C content which is increased, in particular maximized, in the modified nucleic acid molecule, particularly of the at least one RNA of the RNA vaccine encoding at least one antigen in the inventive vaccine/inhibitor combination, with the "frequent" codons without modifying the amino acid sequence of the protein encoded by the coding region of the nucleic acid molecule. This preferred embodiment allows provision of a particularly efficiently translated and stabilized (modified) nucleic acid, particularly of the at least one RNA of the RNA vaccine encoding at least one antigen in the inventive vaccine/inhibitor combination.

Derivative of a nucleic acid molecule: A derivative of a nucleic acid molecule is defined herein in the same manner as a modified nucleic acid, as defined above.

Nucleotide analogues: Nucleotide analogues are nucleotides structurally similar (analogue) to naturally occurring nucleotides which include phosphate backbone modifications, sugar modifications, or modifications of the nucleobase.

UTR modification: A nucleic acid molecule, especially if the nucleic acid is in the form of a coding nucleic acid molecule, particularly the at least one RNA of the RNA vaccine comprising at least one open reading frame coding for at least one antigen according to the invention, preferably has at least one modified 5' and/or 3' UTR sequence (UTR modification). These in the 5' and/or 3' untranslated regions (UTR) included sequences may have the effect of increasing the half-life of the nucleic acid in the cytosol or may increase the translation of the encoded protein or peptide. These UTR sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used for a stabilized nucleic acid. Another example of a stabilizing sequence has the general formula (C/U)CCANxCCC(U/A)PyxUC(C/U)CC which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Particularly preferred in the context of the present invention is the mutated UTR of (alpha-)globin comprising the following sequence GCCCGaTGGG CCTCCCAACG GGCCCTCCTC CCCTCCTTGC ACCG (SEQ ID NO. 1) (the underlined nucleotide shows the mutation compared to the wild type sequence), which is also termed herein as muag. Such introduced UTR sequences can of course be used individually or in combination with one another and also in combination with other sequence modifications known to a person skilled in the art.

Histone stem-loop: In the context of the present invention, a histone stem-loop sequence is preferably selected from at least one of the following formulae (I) or (II):

formula (I) (stem-loop sequence without stem bordering elements):

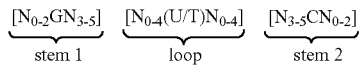

formula (II) (stem-loop sequence with stem bordering elements):

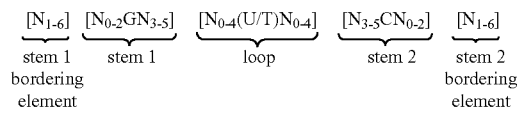

wherein:
stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 [$N_{0-2}GN_{3-5}$] is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof; and wherein G is guanosine or an analogue thereof, and may be optionally replaced by a cytidine or an analogue thereof, provided that its complementary nucleotide cytidine in stem2 is replaced by guanosine;

loop sequence [$N_{0-4}$ (U/T)$N_{0-4}$] is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 [$N_{3-5}CN_{0-2}$] is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

Nucleic acid synthesis: Nucleic acid molecules used according to the invention as defined herein may be prepared using any method known in the art, including synthetic methods such as e.g. solid phase synthesis, in vivo propagation (e.g. in vivo propagation of viruses), as well as in vitro methods, such as in vitro transcription reactions.

For preparation of a nucleic acid molecule, especially if the nucleic acid is in the form of an RNA or mRNA, a corresponding DNA molecule may e.g. be transcribed in vitro. This DNA matrix preferably comprises a suitable promoter, e.g. a T7 or SP6 promoter, for in vitro transcription, which is followed by the desired nucleotide sequence coding for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

RNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence.

Messenger RNA (mRNA): In eukaryotic cells, transcription is typically performed inside the nucleus or the mitochondria. In vivo, transcription of DNA usually results in the so-called premature RNA which has to be processed into so-called messenger RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, a 5'UTR, an open reading frame, a 3'UTR and a poly(A) sequence. In the context of the present invention, an mRNA may also be an artificial molecule, i.e. a molecule not occurring in nature. This means that the mRNA in the context of the present invention may, e.g., comprise a combination of a 5'UTR, open reading frame, 3'UTR and poly(A) sequence, which does not occur in this combination in nature.

Retrovirus: A retrovirus is an RNA virus that is duplicated in a host cell using the reverse transcriptase enzyme to produce DNA from its RNA genome. The DNA is then incorporated into the host's genome by an integrase enzyme. The virus thereafter replicates as part of the host cell's DNA and then undergoes the usual transcription and translational processes to express the genes carried by the virus. Often lentiviruses were used for gene therapy purposes. For safety reasons lentiviral vectors normally do not carry the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase.

Another plasmid contains the genetic material to be delivered by the vector. It is transcribed to produce the single-stranded RNA viral genome which is packaged into the virion, which is used for infection of cells for gene therapy purposes or genetic vaccination.

Virion: Virus particles (known as virions) consist of two or three parts: i) the genetic material (comprising viral genes and optional substituted heterologous genes) made from either DNA or RNA; ii) a protein coat that protects these genes; and in some cases iii) an envelope of lipids that surrounds the protein coat when they are outside a cell.

Self-replicating RNA (Replicons): Self-replicating RNA are delivery vectors based on alphaviruses which have been developed from Semliki Forest virus (SFV), Sindbis (SIN) virus, and Venezuelan equine encephalitis (VEE) virus. Alphaviruses are single stranded RNA viruses in which heterologous genes of interest may substitute for the alphavirus' structural genes. By providing the structural genes in trans, the replicon RNA is packaged into replicon particles (RP) which may be used for gene therapy purposes or genetic vaccination (see for example Vander Veen et al., 2012. Alphavirus replicon vaccines. Animal Health Research Reviews 13(1):1-9). After entry into the host cell, the genomic viral RNA initially serves as an mRNA for translation of the viral nonstructural proteins (nsPs) required for initiation of viral RNA amplification. RNA replication occurs via synthesis of a full-length minus-strand intermediate that is used as the template for synthesis of additional genome-length RNAs and for transcription of a plus-strand subgenomic RNA from an internal promoter. Such RNA may then be considered as self-replicating RNA, since the non-structural proteins responsible for replication (and transcription of the heterologous genes) are still present in such replicon. Such alphavirus vectors are referred to as "replicons."

Replicon particle: A replicon particle consist of two or three parts: i) the genetic material (=the replicon) (comprising viral genes and optional substituted heterologous genes) made from either DNA or RNA; ii) a protein coat that protects these genes; and in some cases iii) an envelope of lipids that surrounds the protein coat when they are outside a cell.

Isolated RNA: Isolated RNA is defined herein as RNA which is not part of a cell, an irradiated cell or a cell lysate. An isolated RNA may be produced by isolation and/or purification from cells or cell lysates, or from in vitro transcription systems.

The term isolated RNA in the context of the present invention is defined herein as RNA which is not part of cells, irradiated cells or cell lysates including the RNA of the RNA vaccine or which is not part of cells transfected with the RNA of the RNA vaccine. In other words, the term "isolated RNA" excludes (ex vivo) transfected or modulated cells used as RNA vaccine, in particular excludes ex vivo transfected or modulated immune cells, such as dendritic cells (DC), e.g. DC transfected/transduced with an RNA used as RNA vaccine. Furthermore, the term isolated RNA excludes RNA comprised in cells, irradiated cells or cell lysate comprising naturally the at least one RNA coding for an antigen used as RNA vaccine. Accordingly, the RNA vaccine of the inventive combination does preferably not comprise modulated or transfected cells, in particular no transfected or modulated immune cells (e.g. antigen presenting cells), more particularly no transfected or modulated DC, irradiated cells or cell lysates comprising naturally the at least one RNA of the RNA vaccine. By that embodiment, it becomes clear that the RNA vaccine used in the present invention does preferably not correspond to a cell-based vaccine or a DC-based vaccine, or, more generally, does preferably not correspond to a cell-based vaccine or, more generally, the RNA vaccine used in the present invention is preferably free of cells and the inventive combination to be administered provides the RNA vaccine as RNA, more preferably as mRNA, optionally in association with a carrier and/or adjuvant component. The term isolated RNA also includes RNA that is complexed with further components e.g. peptides, proteins, carriers etc., RNA packaged in particles like e.g. replicon particles or virus particles (virions) and RNA contained in solution which may additional to the RNA comprise further components e.g. buffer, stabilization reagents, RNAse inhibitors, etc.

Sequence of a nucleic acid molecule: The sequence of a nucleic acid molecule is typically understood to be the particular and individual order, i.e. the succession of its nucleotides.

Sequence of a protein or peptide: The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Fragment of a sequence: a fragment of a sequence is typically a shorter portion of a full-length sequence of e.g. a nucleic acid sequence or an amino acid sequence. Accordingly, a fragment of a sequence, typically, consists of a sequence that is identical to the corresponding stretch or corresponding stretches within the full-length sequence. A preferred fragment of a sequence in the context of the present invention, consists of a continuous stretch of entities, such as nucleotides or amino acids, corresponding to a continuous stretch of entities in the molecule the fragment is derived from, which represents at least 5%, preferably at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived. Thus, for example, a fragment of a protein or peptide antigen preferably corresponds to a continuous stretch of entities in the protein or peptide antigen the fragment is derived from, which represents at least 5%, preferably at least 20%, preferably at least 30%, more preferably at least 40%, more preferably at least 50%, even more preferably at least 60%, even more preferably at least 70%, and most preferably at least 80% of the total (i.e. full-length) protein or peptide antigen. It is particularly preferred that the fragment of a sequence is a functional fragment, i.e. that the fragment fulfils one or more of the functions fulfilled by the sequence the fragment is derived from. For example, a fragment of a protein or peptide antigen preferably exhibits at least one antigenic function (e.g. is capable of eliciting a specific immune reaction against at least one antigen determinant in said protein or peptide antigen) of the protein or peptide antigen the fragment is derived from.

Fragments of proteins: "Fragments" of proteins or peptides, i.e., fragments of amino acid sequences, in the context of the present invention may, typically, comprise a sequence of a protein or peptide as defined herein, which is, with regard to its amino acid sequence (or its encoding nucleic acid molecule), N-terminally, C-terminally and/or intrasequentially truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Likewise, "fragments" of nucleic acid sequences in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

Transfection: The term 'transfection' refers to the introduction of nucleic acid molecules, such as DNA or RNA (e.g. mRNA) molecules, into cells, preferably into eukaryotic cells. In the context of the present invention, the term 'transfection' encompasses any method known to the skilled person for introducing nucleic acid molecules, preferably RNA molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc.

Carrier: A carrier in the context of the invention may typically be a compound that facilitates transport and/or complexation of another compound (cargo). A carrier may be associated to its cargo by covalent or non-covalent interaction. A carrier may transport nucleic acids, e.g. RNA or DNA, to the target cells. The carrier may—for some embodiments—be a cationic or polycationic compound or a polymeric carrier as defined herein. A carrier, in the context of the present invention, is preferably suitable as carrier for nucleic acid molecules, e.g. for mediating dissolution in physiological acceptable liquids, transport and cellular uptake of the nucleic acid molecules or a vector. Accordingly, a carrier, in the context of the present invention, may be a component which may be suitable for depot and delivery of a nucleic acid molecule or vector. Such carriers may be, for example, cationic or polycationic carriers or compounds which may serve as transfection or complexation agent. Particularly preferred carriers or polymeric carriers in this context are cationic or polycationic compounds.

Cationic or polycationic compound/component:

The term "cationic or polycationic compound/component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic or polycationic compound/component may be any positively charged compound or polymer, preferably a cationic or polycationic peptide or protein which is positively charged under physiological conditions, particularly under physiological conditions in vivo. A 'cationic peptide or protein' may contain at least one positively charged amino acid, or more than one positively charged amino acid, e.g. selected from Arg, His, Lys or Orn. Accordingly, 'polycationic' compounds are also within the scope exhibiting more than one positive charge under the conditions given. In this context a cationic peptide or protein contains a larger number of cationic amino acids, e.g. a larger number of Arg, His, Lys or Orn, than negatively charged amino acids. In a preferred embodiment, a cationic peptide or protein in the context of the present invention contains a larger number of cationic amino acids, e.g. a larger number of Arg, His, Lys or Orn, than other residues.

The term "cationic or polycationic compound" in the context of the present invention preferably refers to compounds which can be used as transfection or complexation agent, particularly of nucleic acids, used according to the invention.

Cationic or polycationic compounds according to the invention, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones. Protamine is particularly preferred.

Additionally, preferred cationic or polycationic proteins or peptides used as transfection or complexation agent may be selected from the following proteins or peptides having the following total formula (III):

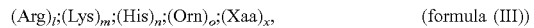

$(Arg)_l;(Lys)_m;(His)_n;(Orn)_o;(Xaa)_x,$ (formula (III))

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, Lipofectamine® or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., block-polymers consisting of a combination of one or more cationic blocks (e.g. selected from a cationic polymer as mentioned above) and of one or more hydrophilic or hydrophobic blocks (e.g. polyethyleneglycole); etc.

Polymeric carrier: A polymeric carrier is typically a carrier that is formed of a polymer. A polymeric carrier in the context of the present invention used as transfection or complexation agent might be a polymeric carrier formed by disulfide-crosslinked cationic components. The disulfide-crosslinked cationic components may be the same or different from each other. The polymeric carrier can also contain further components. It is also particularly preferred that the polymeric carrier comprises mixtures of cationic peptides, proteins or polymers and optionally further components as defined herein, which are crosslinked by disulfide bonds as described herein.

In this context the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex e.g. the at least one RNA of the RNA vaccine encoding at least one antigen or an adjuvant nucleic acid in the inventive vaccine/inhibitor combination contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex e.g. the at least one RNA of the RNA vaccine encoding at least one antigen or an adjuvant nucleic acid in the inventive vaccine/inhibitor combination may be formed by disulfide-crosslinked cationic (or polycationic) components.

According to one first alternative, at least one cationic (or polycationic) component of the polymeric carrier, which may be used in this context may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier, which may be used to complex e.g. the at least one RNA of the RNA vaccine encoding at least one antigen or an adjuvant nucleic acid in the inventive vaccine/inhibitor combination comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moiety, are selected from, without being restricted thereto, following cationic peptides having the following sum formula (IV):

$$\{(Arg)_l;(Lys)_m;(His)_n;(Orn)_o;(Xaa)_x\}; \quad \text{formula (IV)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_3Arg_9His_3$, $His_6Arg_9His_6$, $His_3Arg_4His_3$, $His_6Arg_4His_6$, $TyrSer_2Arg_9Ser_2Tyr$, $(Arg-LysHis)_4$, $Tyr(ArgLysHis)_2Arg$, etc.

According to a one further particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (IV)) as shown above and which comprises or is additionally modified to comprise at least one —SH moiety, may be, without being restricted thereto, selected from subformula (IVa):

$$\{(Arg)_l;(Lys)_m;(His)_n;(Orn)_o;(Xaa')_x(Cys)_y\} \quad \text{formula (IVa)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_l;(Lys)_m;(His)_n;(Orn)_o;(Xaa)_x$ (formula (IV)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (IV)) as shown above, may be, without being restricted thereto, selected from subformula (IVb):

$$Cys^1\{(Arg)_l;(Lys)_m;(His)_n;(Orn)_o;(Xaa)_x\}Cys^2 \quad \text{formula (IVb)}$$

wherein empirical formula $\{(Arg)_l;(Lys)_m;(His)_n;(Orn)_o;(Xaa)_x\}$ (formula (IV)) is as defined herein and forms a core of an amino acid sequence according to (semiempirical) formula (IV) and wherein $Cys^1$ and $Cys^2$ are Cysteines proximal to, or terminal to $(Arg)_l;(Lys)_m;(His)_n;(Orn)_o;(Xaa)_x$. This embodiment may apply to situations, wherein the cationic or polycationic peptide or protein of the polymeric carrier, which may be used to complex the at least one RNA of the RNA vaccine encoding at least one antigen or an adjuvant nucleic acid in the inventive vaccine/inhibitor combination, e.g. when defined according to empirical formula $(Arg)_l;(Lys)_m;(His)_n;(Orn)_o;(Xaa)_x$ (formula (IV)) as shown above, has been modified with at least two cysteines as —SH moieties in the above meaning such that the cationic or polycationic peptide of the inventive polymeric carrier carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier, which may be used to complex e.g. the at least one RNA of the RNA vaccine encoding at least one antigen or an adjuvant nucleic acid in the inventive vaccine/inhibitor combination may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

According to a particularly preferred embodiment, the further component, which may be contained in the polymeric carrier, which may be used to modify the different (short) cationic or polycationic peptides or (non-peptidic) polymers forming basis for the polymeric carrier or the biophysical/biochemical properties of the polymeric carrier as defined herein, is an amino acid component (AA). According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the aforementioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers).

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) of the polymeric carrier may be bound to further components of the polymeric carrier, which may be used to complex e.g. the at least one RNA of the RNA vaccine encoding at least one antigen or an adjuvant nucleic acid in the inventive vaccine/inhibitor with or without using a disulfide linkage.

According to a further and particularly preferred alternative, the amino acid component (AA), may be used to modify the polymeric carrier, particularly the content of cationic components in the polymeric carrier as defined above.

In the context of the present invention, the amino acid component (AA) may be selected from the following alternatives: an aromatic amino acid component, a hydrophilic (and preferably non charged polar) amino acid component, a lipophilic amino acid component, or a weak basic amino acid component.

According to a further alternative, the amino acid component (AA) may be a signal peptide or signal sequence, a localisation signal or sequence, a nuclear localisation signal or sequence (NLS), an antibody, a cell penetrating peptide (e.g. TAT), etc. Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined herein as antigens. According to one alternative, such further functional peptides or proteins may comprise so called cell penetrating peptides (CPPs) or cationic peptides for transportation.

According to a last alternative, the amino acid component (AA) may consist of or may comprise any peptide or protein which can execute any favourable function in the cell. Particularly preferred are peptides or proteins selected from therapeutically active proteins or peptides, from antigens, e.g. tumour antigens, pathogenic antigens (e.g. animal antigens, viral antigens, protozoan antigens, bacterial antigens), from antibodies, from immunostimulatory proteins or peptides, from antigen-specific T cell receptors, or from any other protein or peptide suitable for a specific (therapeutic) application. Particularly preferred are peptide epitopes from those antigen(s) encoded by the at least one RNA of the RNA vaccine encoding at least one antigen in the inventive vaccine/inhibitor combination.

The polymeric carrier, which may be used to complex e.g. the at least one RNA of the RNA vaccine encoding at least one antigen or an adjuvant nucleic acid in the inventive vaccine/inhibitor combination may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

Further, the polymeric carrier may be selected from a polymeric carrier molecule according to generic formula (V):

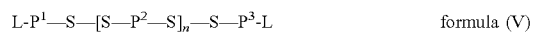

L-P$^1$—S—[S—P$^2$—S]$_n$—S—P$^3$-L    formula (V)

wherein,

P$^1$ and P$^3$ are different or identical to each other and represent a linear or branched hydrophilic polymer chain, each P$^1$ and P$^3$ exhibiting at least one —SH-moiety, capable to form a disulfide linkage upon condensation with component P$^2$, or alternatively with (AA), (AA)$_x$, or [(AA)$_x$]$_z$ if such components are used as a linker between P$^1$ and P$^2$ or P$^3$ and P$^2$) and/or with further components (e.g. (AA), (AA)$_x$, [(AA)$_x$]$_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

p² is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each P² exhibiting at least two —SH-moieties, capable to form a disulfide linkage upon condensation with further components P² or component(s) P¹ and/or P³ or alternatively with further components (e.g. (AA), (AA)$_x$, or [(AA)$_x$]$_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components P¹ and P², P² and P², or P² and P³, or optionally of further components as defined herein (e.g. L, (AA), (AA)$_x$, [(AA)$_x$]$_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

Each of hydrophilic polymers P¹ and P³ typically exhibits at least one —SH-moiety, wherein the at least one —SH-moiety is capable to form a disulfide linkage upon reaction with component P² or with component (AA) or (AA)$_x$, if used as linker between P¹ and P² or P³ and P² as defined below and optionally with a further component, e.g. L and/or (AA) or (AA)$_x$, if two or more —SH-moieties are contained. The following subformulae "P¹—S—S—P²" and "P²—S—S—P³" within generic formula (V) above (the brackets are omitted for better readability), wherein any of S, P¹ and P³ are as defined herein, typically represent a situation, wherein one —SH-moiety of hydrophilic polymers P¹ and P³ was condensed with one —SH-moiety of component P² of generic formula (V) above, wherein both sulphurs of these —SH-moieties form a disulfide bond —S—S— as defined herein in formula (V). These —SH-moieties are typically provided by each of the hydrophilic polymers P¹ and P³, e.g. via an internal cysteine or any further (modified) amino acid or compound which carries a —SH moiety. Accordingly, the subformulae "P¹—S—S—P²" and "P²—S—S—P³" may also be written as "P¹-Cys-Cys-P²" and "P²-Cys-Cys-P³", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers P¹ and P³ may be modified with a —SH moiety, preferably via a chemical reaction with a compound carrying a —SH moiety, such that each of the hydrophilic polymers P¹ and P³ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers P¹ and P³ as defined herein. Such non-amino compounds may be attached to the hydrophilic polymers P¹ and P³ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, □,□ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers P¹ and P³. As defined herein, each of hydrophilic polymers P¹ and P³ typically exhibits at least one —SH— moiety preferably at one terminal end, but may also contain two or even more —SH-moieties, which may be used to additionally attach further components as defined herein, preferably further functional peptides or proteins e.g. a ligand, an amino acid component (AA) or (AA)$_x$, antibodies, cell penetrating peptides or enhancer peptides (e.g. TAT, KALA), etc.

In the context of the entire formula (V) of the inventive polymeric carrier may be preferably defined as follows:

$$L\text{-}P^1\text{—}S\text{-}[Cys\text{-}P^2\text{-}Cys]_n\text{-}S\text{—}P^3\text{-}L \qquad \text{formula (VI)}$$

wherein L, $P^1$, $P^2$, $P^3$ and n are as defined herein, S is sulphur and each Cys provides for one —SH-moiety for the disulfide bond.

The amino acid component (AA) or $(AA)_x$ in the polymeric carrier of formula (V or VI), e.g. as defined above for the polymeric carrier formed by disulfide-crosslinked cationic components may also occur as a mixed repetitive amino acid component $[(AA)_x]_z$, wherein the number of amino acid components (AA) or $(AA)_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values.

According to a specific and particularly preferred alternative, the amino acid component (AA) or $(AA)_x$, preferably written as $S\text{-}(AA)_x\text{-}S$ or $[S\text{-}(AA)_x\text{-}S]$ may be used to modify component $P^2$, particularly the content of component $S\text{-}\alpha^2\text{—}S$ in repetitive component $[S\text{-}\alpha^2\text{—}S]_n$ of the polymeric carrier of formula (V) above. This may be represented in the context of the entire polymeric carrier according to formula (VI) e.g. by following formula (VIa):

$$L\text{-}P^1\text{—}S\text{-}\{[S\text{-}\alpha^2\text{—}S]_a[S\text{-}(AA)_x\text{-}S]_b\}\text{-}S\text{—}P^3\text{-}L, \qquad \text{formula (VIa)}$$

wherein x, S, L, AA, $P^1$, $P^2$ and $P^3$ are preferably as defined herein. In formula (VIa) above, any of the single components $[S\text{-}\alpha^2\text{—}S]$ and $[S\text{-}(AA)_x\text{-}S]$ may occur in any order in the subformula $\{[S\text{-}\alpha^2\text{—}S]_a[S\text{-}(AA)_x\text{-}S]b\}$. The numbers of single components $[S\text{-}\alpha^2\text{—}S]$ and $[S\text{-}(AA)_x\text{-}S]$ in the subformula $\{[S\text{-}\alpha^2\text{—}S]_a[S\text{-}(AA)_x\text{-}S]b\}$ are determined by integers a and b, wherein a+b=n. n is an integer and is defined as above for formula (V).

According to another embodiment, the polymeric carrier, which may be used to complex e.g. the at least one RNA of the RNA vaccine encoding at least one antigen or an adjuvant nucleic acid in the inventive vaccine/inhibitor combination or single components thereof, e.g. of the above mentioned cationic or polycationic peptides, proteins or polymers or further components, e.g. (AA), may be further modified with a ligand, preferably a carbohydrate, more preferably a sugar, even more preferably mannose.

According to one specific embodiment, the entire polymeric carrier may be formed by a polymerization condensation (of at least one) of the above mentioned cationic or polycationic peptides, proteins or polymers or further components, e.g. (AA), via their —SH-moieties in a first step and complexing e.g. the at least one RNA of the RNA vaccine encoding at least one antigen or an adjuvant nucleic acid in the inventive vaccine/inhibitor combination to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific embodiment, the polymeric carrier, which may be used to complex e.g. the at least one RNA of the RNA vaccine encoding at least one antigen or an adjuvant nucleic acid in the inventive vaccine/inhibitor combination is formed by carrying out the polymerization condensation of at least one of the above mentioned cationic or polycationic peptides, proteins or polymers or further components, e.g. (AA), via their —SH-moieties simultaneously to complexing e.g. the at least one RNA of the RNA vaccine encoding at least one antigen or an adjuvant nucleic acid in the inventive vaccine/inhibitor combination to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

N/P ratio: The N/P ratio is a measure of the ionic charge of the cationic (side chain) component of the cationic or polycationic compound or of the polymeric carrier used as carrier or complexation agent as defined herein. In particular, if the cationic properties of the cationic component are generated by nitrogens (e.g. of the amino acid side chains), the N/P ratio expresses the ratio of basic nitrogen atoms to phosphate residues in the nucleotide backbone, considering that (side chain) nitrogen atoms in the cationic component of the cationic or polycationic compound or of the polymeric carrier contribute to positive charges and phosphate of the phosphate backbone of the nucleic acid cargo e.g. the at least one RNA coding for at least one antigen comprised in the RNA vaccine or an adjuvant nucleic acid contribute to the negative charge. Generally, one phosphate provides one negative charge, e.g. one nucleotide in the cargo nucleic acid molecule provides one negative charge. It may be calculated on the basis that, for example, 1 µg RNA typically contains about 3 nmol phosphate residues, provided that RNA exhibits a statistical distribution of bases. Additionally, 1 nmol peptide typically contains about x nmol nitrogen residues, dependent on the molecular weight and the number of its (cationic) amino acids.

Zetapotential: The "zetapotential" is a widely used parameter for the electrical surface charge of a particle. It is typically determined by moving the charged particle through an electrical field. In the context of the present invention, the zetapotential is the preferred parameter for characterizing the charge of a particle, e.g. of a complex comprising as carrier or complexation agent a cationic or polycationic compound and/or a polymeric carrier and as nucleic acid cargo the at least one RNA coding for at least one antigen of the RNA vaccine or an adjuvant nucleic acid. Thus, in the context of the present invention, the charge of a particle is preferably determined by determining the zetapotential by the laser Doppler electrophoresis method using a Zetasizer Nano instrument (Malvern Instruments, Malvern, UK) at 25° C. and a scattering angle of 173°. The surface charge of a given particle also depends on the ionic strength of the utilized matrix (e.g. salt containing buffer) and the pH of the solution. Therefore, the actual zetapotential of a given complex at a charge ratio (N/P) may differ slightly between different buffers used for injection. For the measurement, the particles, such as complexes comprising as carrier or complexation agent a cationic or polycationic compound and/or a polymeric carrier and as nucleic acid cargo the at least one RNA coding for at least one antigen of the RNA vaccine or an adjuvant nucleic acid according to the invention are preferably suspended in Ringer Lactate solution. In a specific embodiment the present invention refers to the use of a negatively charged complex under the conditions of a given injection buffer, preferably under the conditions of a Ringer lactate solution, assessed by its Zetapotential. A Ringer lactate solution according to the present invention preferably contains 130 mmol/L sodium ions, 109 mmol/L chloride ions, 28 mmol/L lactate, 4 mmol/L potassium ions and 1.5 mmol/L calcium ion. The sodium, chloride, potassium and lactate typically come from NaCl (sodium chloride), $NaC_3H_5O_3$ (sodium lactate), $CaCl_2$ (calcium chloride), and KCl (potassium chloride). The osmolarity of the Ringer lactate solution is 273 mOsm/L and the pH is adjusted to 6.5.

Immunostimulatory composition: In the context of the invention, an immunostimulatory composition may be typically understood to be a composition containing at least one component which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one immunostimulating/adjuvant nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Adjuvant nucleic acid: An adjuvant nucleic acid, as used herein, is preferably selected from nucleic acids which are known to bind to TLR receptors. Such an adjuvant nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably, the CpG motifs are unmethylated. Furthermore, an adjuvant nucleic acid, as used herein, can be an immunostimulatory RNA (isRNA), which preferably elicits an innate immune response.

Preferably, an adjuvant nucleic acid, preferably an immunostimulatory RNA (isRNA), as used herein, may comprise any nucleic acid sequence known to be immunostimulatory, including, e.g., nucleic acid sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Such an adjuvant nucleic acid may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, an adjuvant nucleic acid sequence, particularly an isRNA, as used herein, may consist of or comprise a nucleic acid of formula (VII) or (VIII):

$$G_l X_m G_n, \qquad \text{(formula (VII))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n, \qquad \text{(formula (VIII))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The nucleic acids of formula (VII) or (VIII), which may be used as an adjuvant nucleic acid sequence, particularly an isRNA, may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of formula (VII) or (VIII) has a maximum length of e.g. 100 nucleotides, m will typically be <=98. The number of nucleotides G in the nucleic acid of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (VII) according to the invention is preferably not a uracil. Similarly, the number of nucleotides C in the nucleic acid of formula (VIII) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (VIII) according to the invention is preferably not a uracil. Preferably, for formula (VII), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (VIII).

According to a further particularly preferred embodiment, an adjuvant nucleic acid sequence, particularly an isRNA, as used herein, may consist of or comprise a nucleic acid of formula (IX) or (X):

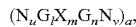
$(N_u G_l X_m G_n N_v)_a$, (formula (IX))

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein
  when l=1, G is guanosine (guanine) or an analogue thereof,
  when l>1, at least 50% of these nucleotides (nucleosides) are guanosine (guanine) or an analogue thereof;
m is an integer and is at least 3;
  wherein
  when m=3, X is uridine (uracil) or an analogue thereof, and
  when m>3, at least 3 successive uridines (uracils) or analogues of uridine (uracil) occur;
n is an integer from 1 to 40,
  wherein
  when n=1, G is guanosine (guanine) or an analogue thereof,
  when n>1, at least 50% of these nucleotides (nucleosides) are guanosine (guanine) or an analogue thereof;
u, v may be independently from each other an integer from 0 to 50,
  preferably wherein when u=0, v≥1, or
    when v=0, u≥1;
wherein the nucleic acid molecule of formula (IX) has a length of at least 50 nucleotides, preferably of at least 100 nucleotides, more preferably of at least 150 nucleotides, even more preferably of at least 200 nucleotides and most preferably of at least 250 nucleotides.

$(N_u C_l X_m C_n N_v)_a$ (formula (X))

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein
  when l=1, C is cytidine (cytosine) or an analogue thereof,
  when l>1, at least 50% of these nucleotides (nucleosides) are cytidine (cytosine) or an analogue thereof;
m is an integer and is at least 3;
  wherein
  when m=3, X is uridine (uracil) or an analogue thereof,
  when m>3, at least 3 successive uridines (uracils) or analogues of uridine (uracil) occur;
n is an integer from 1 to 40,
  wherein
  when n=1, C is cytidine (cytosine) or an analogue thereof,
  when n>1, at least 50% of these nucleotides (nucleosides) are cytidine (cytosine) or an analogue thereof.
u, v may be independently from each other an integer from 0 to 50,
  preferably wherein when u=0, v≥1, or
    when v=0, u≥1;
wherein the nucleic acid molecule of formula (X) according to the invention has a length of at least 50 nucleotides, preferably of at least 100 nucleotides, more preferably of at least 150 nucleotides, even more preferably of at least 200 nucleotides and most preferably of at least 250 nucleotides.

Any of the definitions given above in formulae (VII) and (VIII), e.g. for elements N (i.e. $N_u$ and $N_v$) and X ($X_m$), particularly the core structure as defined above, as well as for integers a, l, m, n, u and v, similarly apply to elements of formula (IX) and (X) correspondingly. The definition of bordering elements $N_u$ and $N_v$ in formula (X) is identical to the definitions given above for $N_u$ and $N_v$ in formula (IX).

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) (single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. Furthermore, (classes of) immunostimulatory RNA molecules, used as a further compound of the inventive vaccine/inhibitor combination, may include any other RNA capable of eliciting an innate immune response. E.g., such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

siRNA: A small interfering RNA (siRNA), is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

In the context of the present invention, siRNAs directed against PD-1, PD-L1 or PD-L2 may thus be double-stranded RNAs (dsRNAs) having a length of from 17 to 29, preferably from 19 to 25, and preferably is at least 90%, more preferably 95% and especially 100% (of the nucleotides of a dsRNA) complementary to a section of the naturally occurring mRNA sequence coding for PD-1, PD-L1 or PD-L2 either to a coding or a non-coding section, preferably a coding section. Such a section of the naturally occurring mRNA sequence may be termed herein a "target sequence" and may be any section of the naturally occurring mRNA coding for PD-1, PD-L1 or PD-L2.

90% complementary means that with a length of a dsRNA described herein of, for example, 20 nucleotides, the dsRNA contain not more than 2 nucleotides showing no complementarity with the corresponding section of the target sequence. The sequence of the double-stranded siRNA used according to the invention is, however, preferably wholly complementary in its general structure with a section of the target sequence. In this context the nucleic acid molecule of the complex may be a dsRNA having the general structure 5'-$(N_{17-29})$-3', preferably having the general structure 5'-$(N_{19-25})$-3', more preferably having the general structure 5'-$(N_{19-24})$-3', or yet more preferably having the general structure 5'-$(N_{21-23})$-3', wherein for each general structure each N is a (preferably different) nucleotide of a section of the target sequence, preferably being selected from a continuous number of 17 to 29 nucleotides of a section of the target sequence, and being present in the general structure 5'-$(N_{17-29})$-3' in their natural order. In principle, all the sections having a length of from 17 to 29, preferably from 19 to 25, base pairs that occur in the target sequence can serve for preparation of a dsRNA as defined herein. Equally, dsRNAs used as siRNAs can also be directed against mRNA sequences that do not lie in the coding region, in particular in the 5' non-coding region of the target sequence, for example, therefore, against non-coding regions of the target sequence having a regulatory function. The target sequence of the dsRNA used as siRNA can therefore lie in the translated and untranslated region of the target sequence and/or in the region of the control elements of the mRNA sequence. The target sequence for a dsRNA used as siRNA directed against PD-1, PD-L1 or PD-L2 can also lie in the overlapping region of untranslated and translated sequence; in particular, the target sequence can comprise at least one nucleotide upstream of the start triplet of the coding region of the mRNA sequence.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed "protein coding region" or "coding region".

IRES (internal ribosomal entry site) sequence: An IRES can function as a sole ribosome binding site, but it can also serve to provide a bi- or even multicistronic RNA as defined herein which codes for several proteins or peptides, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

Fragment or part of an (protein/peptide) antigen: Fragments or parts of a (protein/peptide) antigen in the context of the present invention are typically understood to be peptides corresponding to a continuous part of the amino acid sequence of a (protein/peptide) antigen, preferably having a length of about 6 to about 20 or even more amino acids, e.g. parts as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. Fragments or parts of the (protein/peptide) antigens as defined herein may also comprise epitopes or functional sites of those (protein/peptide) antigens. Preferably, fragments or parts of a (protein/peptide) antigen in the context of the invention are or comprise epitopes, or do have antigenic characteristics, eliciting an adaptive immune response. Therefore, fragments of (protein/peptide) antigens may comprise at least one epitope of those (protein/peptide) antigens. Furthermore, also domains of a (protein/peptide) antigen, like the extracellular domain, the intracellular domain or the transmembrane domain and shortened or truncated versions of a (protein/peptide) antigen may be understood to comprise a fragment of a (protein/peptide) antigen.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by a nucleic acid molecule, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program. A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide, preferably over the full-length sequence that variant is derived from. Analogously, a "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence, preferably over the full-length sequence the variant is derived from.

Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Vehicle: A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

PD-1 pathway: Members of the PD-1 pathway are all proteins which are associated with PD-1 signaling. On the one hand these might be proteins which induce PD-1 signaling upstream of PD-1 as e.g. the ligands of PD-1 PD-L1 and PD-L2 and the signal transduction receptor PD-1. On the other hand these might be signal transduction proteins downstream of PD-1 receptor. Particularly preferred as members of the PD-1 pathway in the context of the present invention are PD-1, PD-L1 and PD-L2.

PD-1 pathway inhibitor: In the context of the present invention, a PD-1 pathway inhibitor is preferably defined herein as a compound capable to impair the PD-1 pathway signaling, preferably signaling mediated by the PD-1 receptor. Therefore, the PD-1 pathway inhibitor may be any inhibitor directed against any member of the PD-1 pathway capable of antagonizing PD-1 pathway signaling. In this context, the inhibitor may be an antagonistic antibody as defined herein, targeting any member of the PD-1 pathway, preferably directed against PD-1 receptor, PD-L1 or PD-L2. This antagonistic antibody may also be encoded by a nucleic acid. Such encoded antibodies are also called "intrabodies" as defined herein. Also, the PD-1 pathway inhibitor may be a fragment of the PD-1 receptor or the PD1-receptor blocking the activity of PD1 ligands. B7-1 or fragments thereof may act as PD1-inhibiting ligands as well. Furthermore, the PD-1 pathway inhibitor may be siRNA (small interfering RNA) or antisense RNA directed against a member of the PD-1 pathway, preferably PD-1, PD-L1 or PD-L2. Additionally, a PD-1 pathway inhibitor may be a protein comprising (or a nucleic acid coding for) an amino acid sequence capable of binding to PD-1 but preventing PD-1 signaling, e.g. by inhibiting PD-1 and B7-H1 or B7-DL interaction. Additionally, a PD-1 pathway inhibitor may be a small molecule inhibitor capable of inhibiting PD-1 pathway signaling, e.g. a PD-1 binding peptide or a small organic molecule.

Antibody: An antibody may be selected from any antibody, e.g. any recombinantly produced or naturally occurring antibodies, known in the art, in particular antibodies suitable for therapeutic, diagnostic or scientific purposes, particularly directed against PD-1, PD-L1 or PD-L2. Herein, the term "antibody" is used in its broadest sense and specifically covers monoclonal and polyclonal antibodies (including, antagonist, and blocking or neutralizing antibodies) and antibody species with polyepitopic specificity. According to the invention, "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, VL, and a C-terminal constant domain, CL. In contrast, the heavy chain of the IgG antibody, for example, is comprised of an N-terminal variable domain, VH, and three constant domains, CH1, CH2 and CH3. Single chain antibodies may be used according to the present invention as well. Antibodies may preferably comprise full-length antibodies, i.e. antibodies composed of the full heavy and full light chains, as described above. However, derivatives of antibodies such as antibody fragments, variants or adducts may also be used as PD-1 pathway inhibitor according to the invention. Antibody fragments may be selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

Polyclonal antibody: Polyclonal antibody typically means mixtures of antibodies directed to specific antigens or immunogens or epitopes of a protein which were generated by immunization of a host organism, such as a mammal, e.g. including goat, cattle, swine, dog, cat, donkey, monkey, ape, a rodent such as a mouse, hamster and rabbit. Polyclonal antibodies are generally not identical, and thus usually recognize different epitopes or regions from the same antigen. Thus, in such a case, typically a mixture (a composition) of different antibodies will be used, each antibody being directed to specific antigens or immunogens or epitopes of a protein, particularly directed to PD-1, PD-L1 or PD-L2.

Monoclonal antibody: The term "monoclonal antibody" herein typically refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed to a single antigenic site. Furthermore, in contrast to conventional (polyclonal) antibody preparations which typically include different antibodies directed to different determinants (epitopes), each monoclonal antibody is directed to a single determinant on the antigen. For example, monoclonal antibodies as defined above may be made by the hybridoma method first described by Kohler and Milstein, Nature, 256:495 (1975), or may be made by recombinant DNA methods, e.g. as described in U.S. Pat. No. 4,816,567. "Monoclonal antibodies" may also be isolated from phage libraries generated using the techniques described in McCafferty et al., Nature, 348:552-554 (1990), for example. According to Kohler and Milstein, an immunogen (antigen) of interest is injected into a host such as a mouse and B-cell lymphocytes produced in response to the immunogen are harvested after a period of time. The B-cells are combined with myeloma cells obtained from mouse and introduced into a medium which permits the B-cells to fuse with the myeloma cells, producing hybridomas. These fused cells (hybridomas) are then placed into separate wells of microtiter plates and grown to produce monoclonal antibodies. The monoclonal antibodies are tested to determine which of them are suitable for detecting the antigen of interest. After being selected, the monoclonal antibodies can be grown in cell cultures or by injecting the hybridomas into mice. In the context of the present invention particularly preferred are monoclonal antibodies directed against PD-1, PD-L1 and PD-L2.

Chimeric antibodies: Chimeric antibodies, which may be used as PD-1 pathway inhibitor according to the invention are preferably antibodies in which the constant domains of an antibody described above are replaced by sequences of antibodies from other organisms, preferably human sequences.

Humanized antibodies: Humanized (non-human) antibodies, which may be used as PD-1 pathway inhibitor according to the invention are antibodies in which the constant and variable domains (except for the hypervariable domains) of an antibody are replaced by human sequences.

Human antibodies: Human antibodies can be isolated from human tissues or from immunized non-human host organisms which are transgene for the human IgG gene locus. Additionally, human antibodies can be provided by the use of a phage display.

Bispecific antibodies: Bispecific antibodies in context of the invention are preferably antibodies which act as an adaptor between an effector and a respective target by two different $F_{a/b}$-domains, e.g. for the purposes of recruiting effector molecules such as toxins, drugs, cytokines etc., targeting effector cells such as CTL, NK cells, makrophages, granulocytes, etc. (see for review: Kontermann R. E., Acta Pharmacol. Sin, 2005, 26(1): 1-9). Bispecific antibodies as described herein are, in general, configured to recognize by two different $F_{a/b}$-domains, e.g. two different antigens, immunogens, epitopes, drugs, cells (or receptors on cells), or other molecules (or structures) as described above. Bispecificity means herewith that the antigen-binding regions of the antibodies are specific for two different epitopes. Thus, different antigens, immunogens or epitopes, etc. can be brought close together, what, optionally, allows a direct interaction of the two components. For example, different cells such as effector cells and target cells can be connected via a bispecific antibody. Encompassed, but not limited, by the present invention are antibodies or fragments thereof which bind, on the one hand, a soluble antigen and, on the other hand, an antigen or receptor e.g. PD-1 or its ligands PD-L1 and PD-L2 on the surface of a cell, e.g. a tumor cell.

Intrabodies: Intrabodies may be antibodies as defined above. These antibodies are intracellular expressed antibodies, and therefore these antibodies may be encoded by nucleic acids to be used for expression of the encoded antibodies. Therefore nucleic acids coding for an antibody, preferably as defined above, particularly an antibody directed against a member of the PD-1 pathway, e.g. PD-1, PD-L1 or PD-L2 may be used as PD-1 pathway inhibitor according to the present invention.

According to a first aspect, the object underlying the present invention is solved by a vaccine/inhibitor combination comprising:
(i) as vaccine an RNA vaccine comprising at least one RNA comprising at least one open reading frame (ORF) coding for at least one antigen, and
(ii) as an inhibitor a composition comprising at least one PD-1 pathway inhibitor.

In the context of the present invention, the term "vaccine/inhibitor combination" preferably means a combined occurrence of an RNA vaccine comprising at least one RNA comprising at least one open reading frame (ORF) coding for at least one antigen and of a composition comprising at least one PD-1 pathway inhibitor. Therefore, this vaccine/inhibitor combination may occur either as one composition, comprising all these components in one and the same mixture (e.g. in a pharmaceutical composition), or may occur as a kit of parts, wherein the different components form different parts of such a kit of parts. This inventive vaccine/inhibitor combination preferably allows to elicit an adaptive immune response (and optional an innate immune response) in a patient to be treated, preferably a mammal, by using as a first component an RNA vaccine, comprising at least one RNA comprising at least one open reading frame encoding at least one antigen, preferably encoding a tumour antigen or a pathogenic antigen. The inhibitor of the inventive vaccine/inhibitor combination, preferably a PD-1 pathway inhibitor may antagonize PD-1 pathway signaling by preferably inhibiting or suppressing signal transduction mediated by the PD-1 receptor. Thus, the administration of the vaccine and the inhibitor may occur either simultaneously or timely staggered, either at the same site of administration or at different sites of administration, as further outlined below. Such a vaccine/inhibitor combination may induce an active immune response and thereby prevents e.g. tumour growth or induces tumour regression. The inventive vaccine/inhibitor combination is thus suitable to effectively stimulate antigen-specific immune responses against cancer and pathogen infected cells. More precisely, the inventive vaccine/inhibitor combination is particularly suitable in the treatment of tumour diseases and infectious diseases which may be associated with an overexpression of PD-1, PD-L1 or PD-L2 and to further improve the immune response against such tumour cells and infected cells.

The invention is therefore based on the surprising finding that the combination of an RNA vaccine and a PD-1 pathway inhibitor shows an extremely advantageous inhibition of tumour growth resulting in enhanced survival which could not be expected from the prior art. Thus, the combined treatment with an RNA vaccine, e.g. coding for a specific antigen (active vaccination) such as a tumour antigen, and with an inhibitor directed to a member of the PD-1 pathway, particularly PD-1 receptor or its ligands PD-L1 and PD-L2, could strongly decrease the harmful impact of a disease to be treated, e.g. the growth rate of a tumour. In this context, the inventors surprisingly found that treatment with an RNA vaccine comprising an RNA coding for a tumor antigen in combination with a PD-1 pathway inhibitor unexpectedly inhibited tumor growth resulting in an improved survival of tumor challenged mice in a synergistic manner as evidenced by the occurrence of 50% complete responses.

As a first component, the inventive vaccine/inhibitor combination includes as a vaccine an RNA vaccine which comprises at least one RNA comprising at least one open reading frame (ORF) coding for at least one antigen, preferably a tumour antigen or a pathogenic antigen.

According to the invention, the RNA vaccine of the inventive vaccine/inhibitor combination preferably comprises at least one RNA comprising at least one open reading frame encoding at least one antigen as defined herein.

The at least one RNA of the RNA vaccine may be selected from any RNA suitable to encode an amino acid sequence, preferably from a messenger RNA (mRNA).

However other forms of RNA may likewise find its application in carrying out the teaching of the present invention. For example, the RNA may be a virus derived RNA such as RNA of a retrovirus or an RNA replicon as defined herein e.g. derived from an alphavirus.

In specific embodiments the at least one RNA of the RNA vaccine does not comprise or does not consist of a lentiviral vector or a adenoviral/adeno-associated vector.

In a specific embodiment, the RNA vaccine comprises or consists of isolated RNA as defined herein.

Furthermore, the at least one RNA of the RNA vaccine of the inventive vaccine/inhibitor combination may be a single- or a double-stranded RNA (which may also be regarded as an RNA (molecule) due to non-covalent association of two single-stranded RNA (molecules)) or a partially double-stranded or partially single stranded RNA, which are at least partially self-complementary (both of these partially double-stranded or partially single stranded RNA molecules are typically formed by a longer and a shorter single-stranded RNA molecule or by two single stranded RNA-molecules, which are about equal in length, wherein one single-stranded RNA molecule is in part complementary to the other single-stranded RNA molecule and both thus form a double-stranded RNA molecule in this region, i.e. a partially double-stranded or partially single stranded RNA). Preferably, the at least one RNA of the RNA vaccine of the inventive vaccine/inhibitor combination may be a single-stranded RNA. Furthermore, the at least one RNA of the RNA vaccine of the inventive vaccine/inhibitor combination may be a circular or linear RNA, preferably a linear RNA. More preferably, the at least one RNA of the RNA vaccine of the inventive vaccine/inhibitor combination may be a (linear) single-stranded RNA.

Preferably, the at least one RNA of the RNA vaccine of the inventive vaccine/inhibitor combination comprises a length of about 5 to about 20000, or 100 to about 20000 nucleotides, preferably of about 250 to about 20000 nucleotides, more preferably of about 500 to about 10000, even more preferably of about 500 to about 5000.

In a particular preferred embodiment of the first aspect of the invention, the at least one RNA of the RNA vaccine comprising at least one open reading frame codes for at least one tumour antigen. In this context tumour antigens are preferably located on the surface of the (tumour) cell. Tumour antigens may also be selected from proteins, which are overexpressed in tumour cells compared to a normal cell (e.g. non-tumor cells). Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens associated with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies.

Further, tumour associated antigens may be classified as tissue-specific antigens, also called melanocyte-specific antigens, cancer-testis antigens and tumour-specific antigens. Cancer-testis antigens are typically understood to be peptides or proteins of germ-line associated genes which may be activated in a wide variety of tumours. Human cancer-testis antigens may be further subdivided into antigens which are encoded on the X chromosome, so-called CT-X antigens, and those antigens which are not encoded on the X chromosome, the so-called (non-X CT antigens). Cancer-testis antigens which are encoded on the X-chromosome comprise, for example, the family of melanoma antigen genes, the so-called MAGE-family. The genes of the MAGE-family may be characterised by a shared MAGE homology domain (MHD). Each of these antigens, i.e. melanocyte-specific antigens, cancer-testis antigens and tumour-specific antigens, may elicit autologous cellular and humoral immune responses. Accordingly, the tumour antigen encoded by the RNA comprised in the RNA vaccine used in the present invention is preferably a melanocyte-specific antigen, a cancer-testis antigen or a tumour-specific antigen, preferably it may be a CT-X antigen, a non-X CT-antigen, a binding partner for a CT-X antigen or a binding partner for a non-X CT-antigen or a tumour-specific antigen, more preferably a CT-X antigen, a binding partner for a non-X CT-antigen or a tumour-specific antigen.

Particular preferred tumour antigens according to the present invention are selected from the list consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-B, NY-ESO-1, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pm1/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, and WT1. Such tumour antigens preferably may be selected from the group consisting of p53, CA125, EGFR, Her2/neu, hTERT, PAP, MAGE-A1, MAGE-A3, Mesothelin, MUC-1, GP100, MART-1, Tyrosinase, PSA, PSCA, PSMA, STEAP-1, VEGF, VEGFR1, VEGFR2, Ras, CEA or WT1, and more preferably from PAP, MAGE-A3, WT1, and MUC-1. Such tumour antigens preferably may be selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), surviving (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), TRP-2 (e.g. TRP-2 according to accession number NM_001922), STEAP1 (Six-transmembrane epithelial antigen of prostate 1), PSCA, PSA, PSMA, etc.

In this context it is particularly preferred that the at least one RNA of the RNA vaccine of the inventive vaccine/inhibitor combination encodes the tumour antigens selected from PCA, PSA, PSMA, STEAP and optional MUC-1, or fragments, variants or derivatives thereof.

In a further particularly preferred embodiment the RNA vaccine of the inventive vaccine/inhibitor combination comprises at least one RNA coding for the tumour antigens selected from NY-ESO-1, MAGE-C1, MAGE-C2, Survivin, optional 5T4 and optional MUC-1, or fragments, variants or derivatives thereof.

Furthermore, tumour antigens also may encompass idiotypic antigens associated with a cancer or tumour disease, particularly lymphoma or a lymphoma associated disease, wherein said idiotypic antigen is an immunoglobulin idiotype of a lymphoid blood cell or a T cell receptor idiotype of a lymphoid blood cell.

In a further particularly preferred embodiment of the first aspect of the invention, the at least one RNA of the RNA vaccine comprises at least one open reading frame coding for at least one pathogenic antigen. Pathogenic antigens are peptide or protein antigens derived from a pathogen associated with infectious disease which are preferably selected from antigens derived from the pathogens *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, *Astroviridae*, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis*, Kuru prion, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, *Microsporidia phylum*, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), *Variola major* or *Variola minor*, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In this context, particularly preferred are antigens from the pathogens selected from Influenza virus, respiratory syncytial virus (RSV), Herpes simplex virus (HSV), human Papilloma virus (HPV), Human immunodeficiency virus (HIV), Plasmodium, *Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus.

The at least one RNA of the RNA vaccine comprising at least one open reading frame coding for at least one antigen according to the first aspect of the present invention may occur as a mono-, di-, or even multicistronic RNA, i.e. an RNA which contains the open reading frame of one, two or more proteins or peptides. Such open reading frames in di-, or even multicistronic RNAs may be separated by at least one internal ribosome entry site (IRES) sequence, e.g. as described herein or by signal peptides which induce the cleavage of the resulting polypeptide which comprises several proteins or peptides.

The at least one RNA of the RNA vaccine of the inventive vaccine/inhibitor combination may be stabilized in order to prevent instability and (fast) degradation of the RNA by various approaches. This instability of RNA is typically due to RNA-degrading enzymes, "RNases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this context in the prior art, which may be utilized as well. E.g., the terminal structure is typically of critical importance particularly for an mRNA. As an example, at the 5' end of naturally occurring mRNAs there is usually a so-called cap structure, which is a modified guanosine nucleotide also called 5 'Cap structure, and at the 3' end is typically a sequence of up to 200 adenosine nucleotides (the so-called poly-A tail).

In a further embodiment, the at least one RNA of the RNA vaccine of the inventive vaccine/inhibitor combination comprises at least one of the following structural elements: a 5' and/or 3'-UTR sequence, preferably a 5' and/or 3'-UTR modification, a 5'Cap structure, a poly(C) sequence, a poly-A tail and/or a polyadenylation signal, preferably as defined herein.

In a further embodiment, the at least one RNA of the RNA vaccine of the inventive vaccine/inhibitor combination preferably comprises at least two of the following structural elements: a 5' and/or 3'-UTR sequence, preferably a 5' and/or 3'-UTR modification (e.g. the mutated sequence of the 3'-UTR of the (alpha)globin gene (muag)); a histone-stem-loop structure, preferably a histone-stem-loop in its 3' untranslated region; a 5'-Cap structure; a poly(C) sequence; a poly-A tail; or a polyadenylation signal, e.g. given a 5'-Cap structure and a histone-stem-loop and, potentially a poly-A-tail.

In this context it is particularly preferred that the at least one RNA of the RNA vaccine encoding at least one antigen comprised in the inventive vaccine/inhibitor combination has the following structure in 5' to 3'-direction:
 a) an optional 5'-UTR sequence comprising a UTR modification
 b) an open reading frame encoding an antigen as defined above;
 c) a 3'-UTR sequence comprising a UTR modification
 d) at least one histone stem-loop, optionally without a histone downstream element 3' to the histone stem-loop
 e) a poly(A) sequence or optional a polyadenylation signal; and
 f) a poly(C) sequence.

In another particular preferred embodiment the at least one RNA of the RNA vaccine encoding at least one antigen in the inventive vaccine/inhibitor combination has the following structure in 5' to 3'-direction:
 a) an optional 5'-UTR sequence comprising a UTR modification
 b) an open reading frame encoding an antigen as defined above;
 c) a 3'-UTR sequence comprising a UTR modification
 d) a poly(A) sequence
 e) a poly(C) sequence; and
 f) at least one histone stem-loop.

For further improvement of the resistance to e.g. in vivo degradation (e.g. by an exo- or endo-nuclease), the at least one RNA of the RNA vaccine encoding at least one antigen in the inventive vaccine/inhibitor combination may be provided as a stabilized nucleic acid, e.g. in the form of a modified nucleic acid as defined herein. According to a further embodiment of the invention, it is therefore preferred that the at least one RNA of the RNA vaccine encoding at least one antigen in the inventive vaccine/inhibitor combination is stabilized, preferably by backbone modifications, sugar modifications and/or base modifications, more preferred stabilized by modification of the G/C-content as defined herein. All of these modifications may be introduced into the at least one RNA without impairing the RNA's function to be translated into the antigen, to be reverse transcribed or to be replicated.

According to another embodiment, the at least one RNA of the RNA vaccine encoding at least one antigen in the inventive vaccine/inhibitor combination may be modified and thus stabilized by modifying the G (guanosine)/C (cytosine) content of the mRNA, preferably of the open reading frame thereof.

Therein, the G/C content of the at least one RNA of the RNA vaccine encoding at least one antigen in the inventive vaccine/inhibitor combination is particularly increased compared to the G/C content of the open reading frame of its particular wild type open reading frame, i.e. the unmodified RNA as defined herein. However, the encoded amino acid sequence of the open reading frame of the at least one RNA of the RNA vaccine encoding at least one antigen in the inventive vaccine/inhibitor combination RNA is preferably not modified compared to the encoded amino acid sequence of the particular wild type open reading frame.

According to a further preferred embodiment of the invention, the at least one RNA of the RNA vaccine encoding at least one antigen in the inventive vaccine/inhibitor combination is optimized for translation (codon-optimized) as defined herein, preferably optimized for translation by replacing codons for less frequent tRNAs of a given amino acid by codons for more frequently occurring tRNAs of the respective amino acid.

In this context, it is particularly preferred to link the sequential G/C content which is increased, in particular maximized, in the at least one RNA of the RNA vaccine encoding at least one antigen in the inventive vaccine/ inhibitor combination, with the "frequent" codons without modifying the amino acid sequence of the protein encoded by the open reading frame comprised in the at least one RNA of the RNA vaccine.

In the context of the present invention, the at least one RNA of the RNA vaccine encoding at least one antigen in the inventive vaccine/inhibitor combination, may be prepared using any method known in the art, including synthetic methods such as e.g. solid phase synthesis, as well as in vivo propagation like e.g. production of virus-like particles or replicon particles in cells or in vitro methods, such as in vitro transcription reactions. Replicons such as self-amplifying RNA based on an alphavirus genome can be produced by constructing DNA plasmids encoding the self-amplifying RNA using standard molecular techniques. Linearized DNA is transcribed in vitro by, for example, T7 RNA polymerase and the resulting RNA is introduced into cells, e.g. by electroporation. Replicon particle production can be evaluated in packaging assays in which in vitro transcribed replicon and defective helper RNA are cotransfected into cells (Perri et al., 2003. J. Virol. 77(19):10394-403; 12970424).

In a further embodiment the RNA vaccine of the inventive vaccine/inhibitor combination comprises a plurality or more than one, preferably 2 to 10, more preferably 2 to 5, most preferably 2 to 4 of RNA molecules as defined herein. These RNA vaccines comprise more than one RNA molecules, preferably encoding different peptides or proteins which comprise preferably different tumour antigens or pathogenic antigens.

In this context it is particularly preferred that the RNA vaccine of the inventive vaccine/inhibitor combination comprising a plurality (which means typically more than 1, 2, 3, 4, 5, 6 or more than 10 nucleic acids, e.g. 2 to 10, preferably 2 to 5 nucleic acids) of RNA molecules, particularly for use in the treatment of prostate cancer (PCa) comprises at least:

a) an RNA molecule encoding at least one peptide or protein, wherein said encoded peptide or protein comprises the tumour antigen PSA, or a fragment, variant or derivative thereof; and b) an RNA molecule encoding at least one peptide or protein, wherein said encoded peptide or protein comprises the tumour antigen PSMA, or a fragment, variant or derivative thereof; and c) an RNA molecule encoding at least one peptide or protein, wherein said encoded peptide or protein comprises the tumour antigen PSCA, or a fragment, variant or derivative thereof;

d) an RNA molecule encoding at least one peptide or protein, wherein said encoded peptide or protein comprises the tumour antigen STEAP-1, or a fragment, variant or derivative thereof; and optional e) an RNA molecule encoding at least one peptide or protein, wherein said encoded peptide or protein comprises the tumour antigen MUC-1, or a fragment, variant or derivative thereof.

In a further preferred embodiment the RNA vaccine of the inventive vaccine/inhibitor combination comprising a plurality (which means typically more than 1, 2, 3, 4, 5, 6 or more than 10 nucleic acids, e.g. 2 to 10, preferably 2 to 5 nucleic acids) of RNA molecules, particularly for use in the treatment of non-small lung cancer (NSCLC) comprises at least:

a) an RNA molecule encoding at least one peptide or protein, wherein said encoded peptide or protein comprises the tumour antigen NY-ESO-1, or a fragment, variant or derivative thereof; and d) an RNA molecule encoding at least one peptide or protein, wherein said encoded peptide or protein comprises the tumour antigen MAGE-C1, or a fragment, variant or derivative thereof; and e) an RNA molecule encoding at least one peptide or protein, wherein said encoded peptide or protein comprises the tumour antigen MAGE-C2, or a fragment, variant or derivative thereof;

f) an RNA molecule encoding at least one peptide or protein, wherein said encoded peptide or protein comprises the tumour antigen Survivin, or a fragment, variant or derivative thereof; and optional g) an RNA molecule encoding at least one peptide or protein, wherein said encoded peptide or protein comprises the tumour antigen 5T4, or a fragment, variant or derivative thereof; and optional h) an RNA molecule encoding at least one peptide or protein, wherein said encoded peptide or protein comprises the tumour antigen MUC-1, or a fragment, variant or derivative thereof.

According to one embodiment of the present invention, the at least one RNA of the RNA vaccine encoding at least one antigen in the inventive vaccine/inhibitor combination may be administered naked without being associated with any further vehicle, transfection or complexation agent for increasing the transfection efficiency and/or the immunostimulatory properties of the at least one RNA.

In a preferred embodiment, the at least one RNA of the RNA vaccine encoding at least one antigen in the inventive vaccine/inhibitor combination may be formulated together with a cationic or polycationic compound and/or with a polymeric carrier as defined herein. Accordingly, in a specific embodiment of the invention it is preferred that the at least one RNA of the RNA vaccine encoding at least one antigen in the inventive vaccine/inhibitor combination is associated with or complexed with a cationic or polycationic compound or a polymeric carrier as defined herein, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of RNA to cationic or polycationic compound and/or with a polymeric carrier; or optionally in an N/P-ratio of at least 0.1, 0.2, 0.3, 0.4, 0.5, 0.75, 1, 1.5 or 2. Preferably, the N/P-ratio lies within a range of about 0.1, 0.3, 0.4, 0.5, 0.75, 1.0, 1.5 or 2 to 20, preferably in a range of about 0.2 (0.5 or 0.75 or 1.0) to 12, more preferably in an N/P-ratio of about 0.4 (0.75 or 1.0) to 10, and even more preferably in an N/P ratio of about 0.4 (0.75 or 1.0) to 5. Most preferably the N/P ratio lies in a ratio between 0.1 and 0.9.

In this context it is preferable that the cationic or polycationic compound or the polymeric carrier used as carrier or complexation agent and the at least one RNA of the RNA vaccine encoding at least one antigen in the inventive vaccine/inhibitor combination as defined herein are provided in an N/P-ratio of at least about 1 or, preferably, of a range of about 1 to 20 for in vitro applications (e.g. in the case cells extracted from the patient would be treated in vitro with the inventive pharmaceutical composition and subsequently administered to the patient).

For in vivo applications, an N/P ratio of at least 0.1 (0.2, 0.3, 0.4, 0.5, 0.6), preferably of a range of about 0.1 (0.2, 0.3, 0.4, 0.5, or 0.6) to 1.5 is preferred. Even more preferred is an N/P ratio range of 0.1 or 0.2 to 0.9 or an N/P ratio range of 0.5 to 0.9.

The N/P ratio significantly influences the surface charge of the resulting complex consisting of cationic or polycationic compounds or of a polymeric carrier and a nucleic acid cargo e.g. the at least one RNA coding for at least one antigen comprised in the RNA vaccine or of an adjuvant nucleic acid. Thus, it is preferable that the resulting polymeric carrier cargo complex is positively charged for in vitro applications and negatively or neutrally charged for in vivo applications. The surface charge of the resulting polymeric carrier cargo complex can be indicated as Zetapotential which may be measured by Doppler electrophoresis method using a Zetasizer Nano (Malvern Instruments, Malvern, UK).

The at least one RNA of the RNA vaccine encoding at least one antigen in the inventive vaccine/inhibitor combination may also be associated with a vehicle, transfection or complexation agent for increasing the transfection efficiency and/or the immunostimulatory properties of the at least one RNA.

In this context, it is particularly preferred that the at least one RNA of the RNA vaccine encoding at least one antigen in the inventive vaccine/inhibitor combination is complexed at least partially with a cationic or polycationic compound and/or a polymeric carrier, preferably cationic proteins or peptides. Partially means that only a part of the at least one RNA is complexed with a cationic compound and that the rest of the at least one RNA of the RNA vaccine is comprised in the inventive vaccine/inhibitor combination in uncomplexed form ("free" or "naked"). Preferably, the ratio of complexed RNA to: uncomplexed RNA in the RNA vaccine of the inventive vaccine/inhibitor combination is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed RNA to free RNA in the RNA vaccine of the inventive vaccine/inhibitor combination is selected from a ratio of about 1:1 (w/w).

The at least one complexed RNA in the RNA vaccine of the inventive vaccine/inhibitor combination, is preferably prepared according to a first step by complexing the at least one RNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed RNA after complexing the RNA. Accordingly, the ratio of the RNA and the cationic or polycationic compound and/or the polymeric carrier in the component of the complexed RNA is typically selected in a range that the RNA is entirely complexed and no free cationic or polycationic compound or polymeric carrier or only a negligibly small amount thereof remains in the composition.

Preferably, the ratio of the at least one RNA (e.g. mRNA) comprising at least one open reading frame coding for at least one antigen to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the RNA to the cationic or polycationic compound and/or the polymeric carrier, preferably as defined herein, in the component of the complexed RNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of cationic or polycationic compound and/or polymeric carrier:RNA, preferably as defined herein, in the complex, and most preferably in a range of about 0.7-1.5, 0.5-1 or 0.7-1, and even most preferably in a range of about 0.3-0.9 or 0.5-0.9 preferably provided that the cationic or polycationic compound in the complex is a cationic or polycationic cationic or polycationic protein or peptide and/or the polymeric carrier as defined above. In this specific embodiment, the complexed RNA is also encompassed in the term "adjuvant component".

In another embodiment, the at least one antigen-providing RNA in the RNA vaccine of the inventive vaccine/inhibitor combination as defined above may be formulated together with an adjuvant. Such an adjuvant may be preferably a further nucleic acid that is not encoding a further antigen but is able to stimulate an unspecific immune response, i.e. innate immune response, by interacting with any part of the innate immune system. Such a nucleic acid stimulating an unspecific immune response is termed herein as "adjuvant nucleic acid".

In this context, an adjuvant nucleic acid preferably comprises or consists of an oligo- or a polynucleotide; more preferably an adjuvant nucleic acid comprising or consisting of an RNA or a DNA; even more preferably such an adjuvant nucleic acid comprising or consisting of an RNA or a DNA being complexed with a cationic or polycationic compound and/or with a polymeric carrier as defined herein; optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ratio of about 3:1 (w/w) to about 2:1 (w/w) of adjuvant nucleic acid to cationic or polycationic compound and/or with a polymeric carrier; or optionally in a nitrogen/phosphate ratio of the cationic or polycationic compound and/or polymeric carrier to adjuvant nucleic acid in the range of about 0.1-10, preferably in a range of about 0.3-4, most preferably in a range of about 0.7-1 or 0.5-1, and even most preferably in a range of about 0.3-0.9 or 0.5-0.9. Such a complexed adjuvant nucleic acid is also encompassed in the term "adjuvant component":

In the specific case that the induction of IFN-α is intended, an N/P ratio of at least 0.1 (0.2, 0.3, 0.4, 0.5, or 0.6) or an N/P ratio range of 0.1 to 1 is preferred or more preferred is an N/P ratio range of 0.1 or 0.2 to 0.9 or an N/P ratio range of 0.5 to 0.9. Otherwise, if the induction of TNFα would be intended, an N/P ratio of 1 to 20 is particularly preferred.

In other words, the RNA vaccine of the vaccine/inhibitor combination according to the invention may comprise the at least one RNA encoding at least one antigen, and a further nucleic acid that is acting as an adjuvant which is called the adjuvant nucleic acid. Of course the RNA vaccine of the inventive vaccine/inhibitor combination is not limited to comprise only one adjuvant nucleic acid but may comprise several different such nucleic acids. Both kinds of nucleic acid, the antigen-encoding RNA and the adjuvant nucleic acid, may be, independently from each other, complexed with a carrier as defined herein. Therefore, a cationic or polycationic compound and/or a polymeric carrier used to complex the at least one RNA of the RNA vaccine encoding at least one antigen or the adjuvant nucleic acid, may be selected from any cationic or polycationic compound and/or polymeric carrier as defined herein.

In case the RNA vaccine of the inventive vaccine/inhibitor combination (or the inventive vaccine/inhibitor combination) comprises an antigen-providing RNA and additionally an adjuvant nucleic acid, the immune response that is evoked by administration of such a vaccine comprises activation of both parts of the immune system, the adaptive immune system as well as the innate immune system.

A substantial factor for a suitable adaptive immune response is the stimulation of different T cell sub-populations. T-lymphocytes are typically divided into two subpopulations, the T-helper 1 cells, in the following Th1-cells, and the T-helper 2 cells, in the following Th2-cells, with which the immune system is capable of destroying intracellular and extracellular pathogens (e.g. antigens). Thereby Th1-cells are responsible for intracellular pathogen destruction by assisting the cellular immune response by activation of macrophages and cytotoxic T cells. Th2-cells, on the other hand, are mainly for extracellular pathogen-elimination and promote the humoral immune response by stimulation of B-cells for conversion into plasma cells and by formation of antibodies (e.g. against antigens). The two T-helper cell populations differ in the pattern of the effector proteins (cytokines) produced by them.

The Th1-cell/Th2-cell ratio is of great importance in the induction and maintenance of an adaptive immune response. In connection with the present invention, the Th1-cell/Th2-cell ratio of the (adaptive) immune response is preferably shifted in the direction towards the cellular response (Th1 response) and a cellular immune response is thereby induced. Stimulation of this response of the adaptive immune system is mainly provoked by the translation of the antigen-providing RNA and the resulting presence of the peptide or protein antigens within the organism.

The innate immune system which may support such an adaptive immune response and which may induce or support a shift towards a Th1 response may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc.

In the context of the invention, the activation of the innate immune system can be provided by an adjuvant nucleic acid, preferably an immunostimulatory RNA (isRNA) as defined herein, comprised in the inventive vaccine/inhibitor combination, preferably comprised in the RNA vaccine.

According to the above, in a further preferred embodiment of the invention, the RNA vaccine of the inventive vaccine/inhibitor combination is formulated to comprise
a) said at least one RNA comprising at least one open reading frame coding for at least one antigen; preferably in form of a mono-, bi- or multicistronic RNA, optionally being stabilized, optionally being optimized for translation and/or optionally being complexed with a cationic or polycationic compound or a polymeric carrier;
b) optionally an adjuvant component, comprising or consisting of said at least one RNA comprising at least one open reading frame coding for at least one antigen and/or at least one adjuvant nucleic acid, complexed with a cationic or polycationic compound and/or with a polymeric carrier, and
c) optionally a pharmaceutically acceptable carrier as defined herein.

In this context, it is particularly preferred that the optionally comprised adjuvant component comprises the same RNA as comprised in the RNA vaccine of the inventive vaccine/inhibitor combination as antigen-providing RNA e.g. mRNA coding for at least one antigen.

Furthermore, the RNA vaccine of the inventive vaccine/inhibitor combination may comprise further components for facilitating administration and uptake of the components of the RNA vaccine. Such further components may be an appropriate carrier or vehicle, or e.g. additional adjuvants for supporting any immune response as defined herein.

According to one further embodiment, the components of the RNA vaccine e.g. the at least one RNA coding for at least one antigen and an adjuvant component, of the inventive vaccine/inhibitor combination, may be formulated together or separately in the same or different compositions.

As a second component, the inventive vaccine/inhibitor combination includes as inhibitor a composition comprising a PD-1 pathway inhibitor targeting any member of the PD-1 signaling pathway, preferably targeting PD-1, PD-L1 or PD-L2.

Programmed Death-1 (PD-1, PDCD1) is a type I transmembrane protein belonging to the extended CD28 family of T cell regulators. PD-1 lacks the membrane-proximal cysteine residue required for homodimerization of other members of the CD28 family. Structural and biochemical analyses showed that PD-1 is monomeric in solution as well as on the cell surface (Okazaki and Honjo, 2007. Int Immunol. 19(7):813-24). PD-1 is expressed on activated T cells, B cells and monocytes. The broader expression of PD-1 contrasts with restricted expression of other CD28 family members to T cells, suggesting that PD-1 regulates a wider spectrum of immune responses compared with other CD28 family members.

PD-1 negatively regulates antigen receptor signaling by recruiting the protein tyrosine phosphatase SHP-2 upon interacting with either of two ligands, PD-L1 or PD-L2.

PD-L1 (B7-H1, CD274) and PD-L2 (B7-DC, CD273) are type I transmembrane glycoproteins composed of IgC- and IgV-type extracellular domains. PD-L1 and PD-L2 share 40% amino acid identity while human and mouse orthologs of PD-L1 and PD-L2 share 70% amino acid identity. Both PD-L1 and PD-L2 have short cytoplasmic tails with no known motif for signal transduction, suggesting that these ligands do not transduce any signal upon interaction with PD-1.

The interaction of PD-L1 and PD-1 provides a crucial negative co-stimulatory signal to T cells and functions as cell death inducer. Interaction between low concentration of PD-1 and PD-L1 leads to the transmission of an inhibitory signal that inhibits the proliferation of antigen-specific CD8+ cells. At higher concentrations this interaction does not inhibit T cell proliferation but reduces the production of multiple cytokines. Thus, binding to PD-L1 can antagonize the B7-CD28 signal when antigenic stimulation is weak and plays a key role in downregulating T cell responses.

The role of PD-1 and PD-1 ligands in inhibiting T cell activation and proliferation suggested that these proteins may serve as therapeutic targets for treatments of inflammation, cancer or infectious diseases. Depending on the desired therapeutic outcome, an up- or down-modulation of the PD-1 pathway is required. Up-modulation of the immune system is particularly required in the treatment of cancers and chronic infections. This can be achieved for example by PD-1 blockade or inhibiting the PD-1 pathway. Inhibition of the PD-1 pathway can be achieved, for example, by an antibody directed at PD-1 or a PD-1 ligand. In this context the PD-1 pathway inhibitor may remove T cell dysfunction resulting from PD-1 signaling and thereby restore or enhance T cell function (e.g. proliferation, cytokine production, target cell killing). In addition, anergic T cells which are unresponsive to antigen stimulation may be reactivated.

In the context of the present invention, the PD-1 pathway inhibitor may be in specific embodiments an antibody, particularly an antagonistic antibody or a nucleic acid-encoded antibody (intrabody), an siRNA, an antisense RNA, a protein comprising (or a nucleic acid coding for) an amino acid sequence capable of binding to PD-1 but preventing PD-1 signaling (e.g. a fusion protein of a fragment of PD-L1 or PD-L2 and the Fc part of an immunoglobulin), a soluble protein (or a nucleic acid coding for a soluble protein) competing with membrane-bound PD-1 for binding of its ligands PD-L1 and PD-L2; or a small molecule inhibitor capable of inhibiting PD-1 pathway signaling.

Therefore, in a preferred embodiment of the present invention, the PD-1 pathway inhibitor is an antibody (or a nucleic acid coding for an antibody) directed against PD-1, preferably an antibody specifically binding to the extracellular domain of PD-1 and thereby inhibiting PD-1 signaling. Preferably, such an antagonistic antibody binds close to the PD-L1 binding site on PD-1, thus inhibiting the binding of PD-L1 to PD-1.

Particularly preferred are the anti-PD1 antibodies Nivolumab (MDX-1106/BMS-936558/ONO-4538), (Brahmer et al., 2010. J Clin Oncol. 28(19):3167-75; PMID: 20516446); Pidilizumab (CT-011), (Berger et al., 2008. Clin Cancer Res. 14(10):3044-51; PMID: 18483370); and MK-3475 (SCH 900475).

In a further preferred embodiment, the PD-1 pathway inhibitor is an antibody (or a nucleic acid coding for an antibody) directed against a PD-1 ligand, preferably an antibody specifically binding to the extracellular domain of the PD-1 or PD-2 ligand. Preferably, such antibody binds proximal to and disruptive of the PD-1 or PD-2 binding site on the ligand.

Particularly preferred are the anti-PD-L1 antibodies MDX-1105/BMS-936559 (Brahmer et al. 2012. N Engl J Med. 366(26):2455-65; PMID: 22658128); MPDL3280A/RG7446, or MEDI4736.

In a further preferred embodiment, the PD-1 pathway inhibitor is a protein comprising (or a nucleic acid coding for) an amino acid sequence capable of binding to PD-1 but preventing PD-1 pathway signaling, particularly preferred in this context is a fusion protein of a fragment of PD-L1 or PD-L2 ligand.

In this context, a particularly preferred embodiment is a fusion protein comprising the extracellular domain of PD-L1 or PD-L2 or a fragment thereof capable of binding to PD-1 and an Fc portion of an immunoglobulin. An example of such a fusion protein is represented by AMP-224 (extracellular domain of murine PD-L2/B7-DC fused to the unmodified Fc portion of murine IgG2a protein; Mkrtichyan et al., 2012. J Immunol. 189(5):2338-47; PMID: 22837483).

In the context of the present invention, the administration of the vaccine and the inhibitor may occur either simultaneously or timely staggered, either at the same site of administration or at different sites of administration, as further outlined below.

To ensure that the separate mechanisms elicited by the RNA vaccine and the PD-1 pathway inhibitor are not negatively influenced by each other, the PD-1 pathway inhibitor and the RNA vaccine are preferably administered separated in time (in a time-staggered manner), i.e. sequentially, and/or are administered at different administration sites. This means that the RNA vaccine may be administrated e.g. prior, concurrent or subsequent to the PD-1 pathway inhibitor, or vice versa. Alternatively or additionally, the RNA vaccine and the PD-1 pathway inhibitor may be administered at different administration sites, or at the same administration site, preferably, when administered in a time staggered manner. According to a particularly preferred embodiment, the RNA vaccine is to be administered first and the PD-1 pathway inhibitor is to be administered subsequent to the RNA vaccine. This procedure ensures that the immune cells such as antigen-presenting cells and T cells have already encountered the antigen before the immune system is stimulated by inhibition of the PD-1 pathway, even though a concurrent administration or an administration, wherein the PD-1 pathway inhibitor is to be administered prior to the RNA vaccine, may lead to the same or at least comparable results.

Accordingly, in a further embodiment, the inventive vaccine/inhibitor combination furthermore comprises a pharmaceutically acceptable carrier and/or vehicle.

Such a pharmaceutically acceptable carrier typically includes the liquid or non-liquid basis of a composition comprising the components of the inventive vaccine/inhibitor combination. If the composition is provided in liquid form, the carrier will preferably be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the vaccine/inhibitor combination according to the invention. The term "compatible" as used here means that these constituents of the vaccine/inhibitor combination are capable of being mixed with the RNA vaccine and/or the PD-1 pathway inhibitor in such a manner that no interaction occurs which would substantially reduce the pharmaceutical effectiveness of the vaccine/inhibitor combination under typical use conditions.

Furthermore, the inventive vaccine/inhibitor combination may comprise one or more additional adjuvants which are suitable to initiate or increase an immune response of the innate immune system, i.e. a non-specific immune response, particularly by binding to pathogen-associated molecular patterns (PAMPs). With other words, when administered, the RNA vaccine preferably elicits an innate immune response due to the adjuvant, optionally contained therein. Nevertheless, the adjuvant may also be part of another component of the inventive vaccine/inhibitor combination than the RNA vaccine. Preferably, such an adjuvant may be selected from an adjuvant known to a skilled person and suitable for the present case, i.e. supporting the induction of an innate immune response in a mammal, e.g. an adjuvant nucleic acid or an adjuvant component as defined above or an adjuvant as defined in the following.

Therefore, such an adjuvant may also be selected from any adjuvant known to a skilled person and suitable for the present case, i.e. supporting the induction of an innate immune response in a mammal and/or suitable for depot delivery of the components of the inventive vaccine/inhibitor combination. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methylpropyl)-1H-imidazo [4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (□-glucan); PLGA, PGA and PLA (homo- and co-polymers of lactic acid and glycolic acid; micro spheres/nano spheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo [4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

An adjuvant is preferably selected from adjuvants, which support induction of a Th1-immune response or maturation of naïve T-cells, such as GM-CSF, IL-12, IFNg, any adjuvant nucleic acid as defined above, preferably an immunostimulatory RNA, CpG DNA, etc.

In a further preferred embodiment, it is also possible that the inventive vaccine/inhibitor combination contains besides the antigen-providing RNA and the PD-1 pathway inhibitor further components which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

Accordingly, in another preferred embodiment, the inventive vaccine/inhibitor combination furthermore comprises at least one adjuvant, an auxiliary substance selected from lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an adjuvant nucleic acid, an immunostimulatory RNA (isRNA), a CpG-DNA, an antibacterial agent, or an anti-viral agent.

The vaccine/inhibitor combination as defined according to the present invention may furthermore comprise further additives or additional compounds. Further additives which may be included in the inventive vaccine/inhibitor combination, such as in the RNA vaccine and/or the composition comprising a PD-1 pathway inhibitor, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent.

The inventive vaccine/inhibitor combination typically comprises a "safe and effective amount" of the components of the inventive vaccine/inhibitor combination as defined herein. As used herein, a "safe and effective amount" preferably means an amount of the components, preferably of the at least one RNA encoding at least one antigen and the PD-1 pathway inhibitor, that is sufficient to significantly induce a positive modification or prevention of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The inventive vaccine/inhibitor combination may be administered orally, parenterally, by inhalation spray, topically, rectally, nasally, buccally, vaginally or via an implanted reservoir. The term parenteral as used herein includes subcutaneous, intravenous, intramuscular, intra-articular, intra-nodal, intra-synovial, intrasternal, intrathecal, intrahepatic, intralesional, intracranial, transdermal, intradermal, intrapulmonal, intraperitoneal, intracardial, intraarterial, and sublingual injection or infusion techniques. Preferably the RNA vaccine is administered by intradermal or intramuscular application and the PD-1 pathway inhibitor is preferably administered by intramuscular or intraperitoneal injection, more preferably by intravenous infusion, in case it is in form of an antibody.

According to a further aspect, the object underlying the present invention is solved by a pharmaceutical composition comprising a vaccine and an inhibitor, in particular as vaccine an RNA vaccine comprising at least one RNA comprising at least one open reading frame coding for at least one antigen and as an inhibitor a composition comprising a PD-1 pathway inhibitor, both preferably as defined above. Likewise, the pharmaceutical composition is preferably formulated and administered as defined above for the components of the inventive vaccine/inhibitor combination. Such a pharmaceutical composition may further comprise any ingredient as defined above for the inventive vaccine/inhibitor combination.

Accordingly, the combination of the RNA vaccine and the PD-1 pathway inhibitor as defined according to the present invention may occur either as one composition, e.g. the pharmaceutical composition according to the present invention, or may occur in more than one compositions, e.g. as a kit of parts, wherein the different components form different parts of such kit of parts. These different components, such as the vaccine and the inhibitor, may be formulated each as a pharmaceutical composition or as a composition as defined above. Preferably, each of the different parts of the kit comprises a different component, e.g. one part comprises the RNA vaccine as defined herein, one further part comprises the PD-1 pathway inhibitor as defined herein, etc.

Therefore, according to a further aspect, the present invention also provides kits, particularly kits of parts. Such kits, particularly kits of parts, typically comprise as components alone or in combination with further components as defined herein an RNA vaccine comprising at least one RNA comprising at least one open reading frame coding for at least one antigen and, preferably in a different part of the kit, a PD-1 pathway inhibitor as defined herein. The inventive vaccine/inhibitor combination as defined herein, optionally in combination with further components as defined herein, such as an additional adjuvant, may occur in one or different parts of the kit. As an example, e.g. at least one part of the kit may comprise the RNA vaccine comprising at least one RNA encoding at least one antigen as defined herein, at least one further part of the kit may comprise the PD-1 pathway inhibitor as defined herein, and optionally at least one further part of the kit may comprise an additional adjuvant as described herein. The kit or kit of parts may furthermore contain technical instructions with information on the administration and dosage of the inventive vaccine/inhibitor combination, the inventive pharmaceutical composition or of any of its components or parts.

The inventive vaccine/inhibitor combination, the inventive pharmaceutical composition or the inventive kit of parts comprising an RNA vaccine and a PD-1 pathway inhibitor may be used for human and also for veterinary medical purposes, preferably for human medical purposes.

Therefore, according to a further aspect, the present invention is directed to the first medical use of the inventive vaccine/inhibitor combination, the inventive pharmaceutical composition and the inventive kit of parts comprising an RNA vaccine and a PD-1 pathway inhibitor as defined herein. Accordingly, the inventive vaccine/inhibitor combination, the inventive pharmaceutical composition and the inventive kit of parts comprising an RNA vaccine and a PD-1 pathway inhibitor as defined herein may be used as a medicament.

According to another aspect, the present invention is directed to the second medical use of the inventive vaccine/inhibitor combination, the inventive pharmaceutical composition and the inventive kit of parts comprising an RNA vaccine and a PD-1 pathway inhibitor as defined herein. Thus, the inventive vaccine/inhibitor combination, the inventive pharmaceutical composition and the inventive kit of parts comprising an RNA vaccine and a PD-1 pathway inhibitor as defined herein may be used for the treatment and/or amelioration of various diseases, particularly of cancer and tumor diseases and infectious diseases as defined herein.

Cancer or tumour diseases in this context preferably include e.g. melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma), heptatitis B-induced tumors (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma (=oesophageal cancer), wart involvement, tumors of the small intestine, craniopharyngeomas, ovarian carcinoma, genital tumors, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumor, prostate cancer (=prostate tumors), etc.

In specific embodiments the treatment of lung cancer (e.g. non-small cell lung cancer or small cell lung cancer) or prostate cancer is particularly preferred.

Infectious diseases in this context, preferably includes viral, bacterial or protozoological infectious diseases. Such infectious diseases, preferably (viral, bacterial or protozoological) infectious diseases, are typically selected from the list consisting of Acinetobacter infections, African sleeping sickness (African trypanosomiasis), AIDS (Acquired immunodeficiency syndrome), Amoebiasis, Anaplasmosis, Anthrax, Appendicitis, Arcanobacterium haemolyticum infections, Argentine hemorrhagic fever, Ascariasis, Aspergillosis, Astrovirus infections, Athlete's foot, Babesiosis, Bacillus cereus infections, Bacterial meningitis, Bacterial pneumonia, Bacterial vaginosis (B V), Bacteroides infections, Balantidiasis, Baylisascaris infections, Bilharziosis, BK virus infections, Black piedra, Blastocystis hominis infections, Blastomycosis, Bolivian hemorrhagic fever, Borrelia infectionss (Borreliosis), Botulism (and Infant botulism), Bovine tapeworm, Brazilian hemorrhagic fever, Brucellosis, Burkholderia infections, Buruli ulcer, Calicivirus infections (Norovirus and Sapovirus), Campylobacteriosis, Candidiasis (Candidosis), Canine tapeworm infections, Cat-scratch disease, Chagas Disease (American trypanosomiasis), Chancroid, Chickenpox, Chlamydia infections, Chlamydia trachomatis infections, Chlamydophila pneumoniae infections, Cholera, Chromoblastomycosis, Climatic bubo, Clonorchiasis, Clostridium difficile infections, Coccidioidomycosis, Cold, Colorado tick fever (CTF), Common cold (Acute viral rhinopharyngitis; Acute coryza), Condyloma acuminata, Conjunctivitis, Creutzfeldt-Jakob disease (CJD), Crimean-Congo hemorrhagic fever (CCHF), Cryptococcosis, Cryptosporidiosis, Cutaneous larva migrans (CLM), Cutaneous Leishmaniosis, Cyclosporiasis, Cysticercosis, Cytomegalovirus infections, Dengue fever, Dermatophytosis, Dientamoebiasis, Diphtheria, Diphyllobothriasis, Donavanosis, Dracunculiasis, Early summer meningoencephalitis (FSME), Ebola hemorrhagic fever, Echinococcosis, Ehrlichiosis, Enterobiasis (Pinworm infections), Enterococcus infections, Enterovirus infections, Epidemic typhus, Epiglottitis, Epstein-Barr Virus Infectious Mononucleosis, Erythema infectiosum (Fifth disease), Exanthem subitum, Fasciolopsiasis, Fasciolosis, Fatal familial insomnia (FFI), Fifth disease, Filariasis, Fish poisoning (Ciguatera), Fish tapeworm, Flu, Food poisoning by Clostridium perfringens, Fox tapeworm, Free-living amebic infections, Fusobacterium infections, Gas gangrene, Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infections, Group B streptococcal infections, Haemophilus influenzae infections, Hand foot and mouth disease (HFMD), Hantavirus Pulmonary Syndrome (HPS), Helicobacter pylori infections, Hemolytic-uremic syndrome (HUS), Hemorrhagic fever with renal syndrome (HFRS), Henipavirus infections, Hepatitis A, Hepatitis B, Hepatitis C, Hepatitis D, Hepatitis E, Herpes simplex, Herpes simplex type I, Herpes simplex type II, Herpes zoster, Histoplasmosis, Hollow warts, Hookworm infections, Human bocavirus infections, Human ewingii ehrlichiosis, Human granulocytic anaplasmosis (HGA), Human metapneumovirus infections, Human monocytic ehrlichiosis, Human papillomavirus (HPV) infections, Human parainfluenza virus infections, Hymenolepiasis, Influenza, Isosporiasis, Japanese encephalitis, Kawasaki disease, Keratitis, Kingella kingae infections, Kuru, Lambliasis (Giardiasis), Lassa fever, Legionellosis (Legionnaires' disease, Pontiac fever), Leishmaniasis, Leprosy, Leptospirosis, Lice, Listeriosis, Lyme borreliosis, Lyme disease, Lymphatic filariasis (Elephantiasis), Lymphocytic choriomeningitis, Malaria, Marburg hemorrhagic fever (MHF), Marburg virus, Measles, Melioidosis (Whitmore's disease), Meningitis, Meningococcal disease, Metagonimiasis, Microsporidiosis, Miniature tapeworm, Miscarriage (prostate inflammation), Molluscum contagiosum (MC), Mononucleosis, Mumps, Murine typhus (Endemic typhus), Mycetoma, Mycoplasma hominis, Mycoplasma pneumonia, Myiasis, Nappy/diaper dermatitis, Neonatal conjunctivitis (Ophthalmia neonatorum), Neonatal sepsis (Chorioamnionitis), Nocardiosis, Noma, Norwalk virus infections, Onchocerciasis (River blindness), Osteomyelitis, Otitis media, Paracoccidioidomycosis (South American blastomycosis), Paragonimiasis, Paratyphus, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Pfeiffer's glandular fever, Plague, Pneumococcal infections, Pneumocystis pneumonia (PCP), Pneumonia, Polio (childhood lameness), Poliomyelitis, Porcine tapeworm, Prevotella infections, Primary amoebic meningoencephalitis (PAM), Progressive multifocal leukoencephalopathy, Pseudo-croup, Psittacosis, Q fever, Rabbit fever, Rabies, Rat-bite fever, Reiter's syndrome, Respiratory syncytial virus infections (RSV), Rhinosporidiosis, Rhinovirus infections, Rickettsial infections, Rickettsialpox, Rift Valley fever (RVF), Rocky mountain spotted fever (RMSF), Rotavirus infections, Rubella, Salmonella paratyphus, Salmonella typhus, Salmonellosis, SARS (Severe Acute Respiratory Syndrome), Scabies, Scarlet fever, Schistosomiasis (Bilharziosis), Scrub typhus, Sepsis, Shigellosis (Bacillary dysentery), Shingles, Smallpox (Variola), Soft chancre, Sporotrichosis, Staphylococcal food poisoning, Staphylococcal infections, Strongyloidiasis, Syphilis, Taeniasis, Tetanus, Three-day fever, Tick-borne encephalitis, Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM) and Visceral Larva Migrans (VLM)), Toxoplasmosis, Trichinellosis, Trichomoniasis, Trichuriasis (Whipworm infections), Tripper, Trypanosomiasis (sleeping sickness), Tsutsugamushi disease, Tuberculosis, Tularemia, Typhus, Typhus fever, Ureaplasma urealyticum infections, Vaginitis (Colpitis), Variant Creutzfeldt-Jakob disease (vCJD, nvCJD), Venezuelan equine encephalitis, Venezuelan hemorrhagic fever, Viral pneumonia, Visceral Leishmaniosis, Warts, West Nile Fever, Western equine encephalitis, White piedra (Tinea blanca), Whooping cough, Yeast fungus spots, Yellow fever, Yersinia pseudotuberculosis infections, Yersiniosis, and Zygomycosis.

Particularly preferred are diseases, particularly cancer or tumor diseases, which are associated with an overexpression of at least one member of the PD-1 pathway, preferably PD-1 receptor and/or its ligands PD-L1 and PD-L2.

Particularly preferred in this context is the treatment of melanoma, glioblastoma, and carcinomas of the pancreas, lung, breast, colon, ovary, and renal cells, urothelial cancers, squamous cell carcinomas of the head and neck and hepatocellular carcinoma which are associated with an overexpression of PD-L1. Most particularly preferred is the treatment of non-small cell lung cancer (NSCLC) or small cell lung cancer associated with an overexpression of any member of the PD-1 pathway, particularly of PD-1 or PD-L1.

In another embodiment the treatment of cancer or tumor diseases associated with no or low expression of at least one member of the PD-1 pathway, preferably PD-1 receptor and/or its ligands PD-L1 and PD-L2 is particularly preferred. In this context the RNA vaccine of the inventive vaccine/inhibitor combination is able to induce the expression of at least one member of the PD-1 pathway, e.g. PD-L1 in the patient to be treated and therefore enables the therapeutic activity of the PD-1 inhibitor.

According to another aspect, the present invention provides a PD-1 pathway inhibitor as defined above, for use in therapy in combination with an RNA vaccine comprising at least one RNA comprising at least one open reading frame coding for at least one antigen as defined above, for example, for use in a method of treatment or prevention of tumor and/or cancer diseases or infectious diseases as defined herein.

According to yet another aspect, the present invention provides an RNA vaccine comprising at least one RNA comprising at least one open reading frame coding for at least one antigen as defined above, for use in therapy in combination with a PD-1 pathway inhibitor as defined above, for example, for use in a method of treatment or prevention of tumor and/or cancer diseases or infectious diseases as defined herein.

Furthermore, the present invention provides in a further aspect a method for transfecting and/or treating a cell, a tissue or an organism, thereby applying or administering the inventive vaccine/inhibitor combination particularly for therapeutic purposes. In this context, typically after preparing the inventive vaccine/inhibitor combination, the inventive vaccine/inhibitor combination is preferably administered to a cell, a tissue or an organism, preferably using any of the administration modes as described herein. The method for transfecting and/or treating a cell may be carried out in vitro, in vivo or ex vivo.

Therefore, the invention also provides a method of treatment comprising administering to a subject in need thereof a therapeutically effective amount of an RNA vaccine comprising at least one RNA comprising at least one open reading frame coding for at least one antigen as defined above in combination with a composition comprising a PD-1 pathway inhibitor as defined above.

In a preferred embodiment, the method comprises the in vitro transfection of isolated cells. The cells used therefore are preferably human or animal cells, particularly cells of a primary cell culture, which are then retransferred to a human or animal. Prior to transfection, these cells are typically isolated from the patient to be treated and cultivated.

In a further preferred embodiment, the method of treatment does not comprise the in vitro transfection of isolated cells. In this case, the RNA vaccine as defined above administered to the subject in need thereof does not comprise isolated cells transfected with the at least one RNA comprising at least one open reading frame coding for at least one antigen comprised in the RNA vaccine.

In the present invention, if not otherwise indicated, different features of alternatives and embodiments may be combined with each other. In the context of the present invention, term "comprising" may be substituted with the term "consisting of", where applicable.

BRIEF DESCRIPTION OF THE FIGURES

The figures shown in the following are merely illustrative and shall describe the present invention in a further way. These figures shall not be construed to limit the present invention thereto.

FIG. 3: G/C optimized mRNA sequence of R1710 coding for *Gallus gallus* ovalbumin as comprised in the OVA-RNActive vaccine.

EXAMPLES

Figure 1:
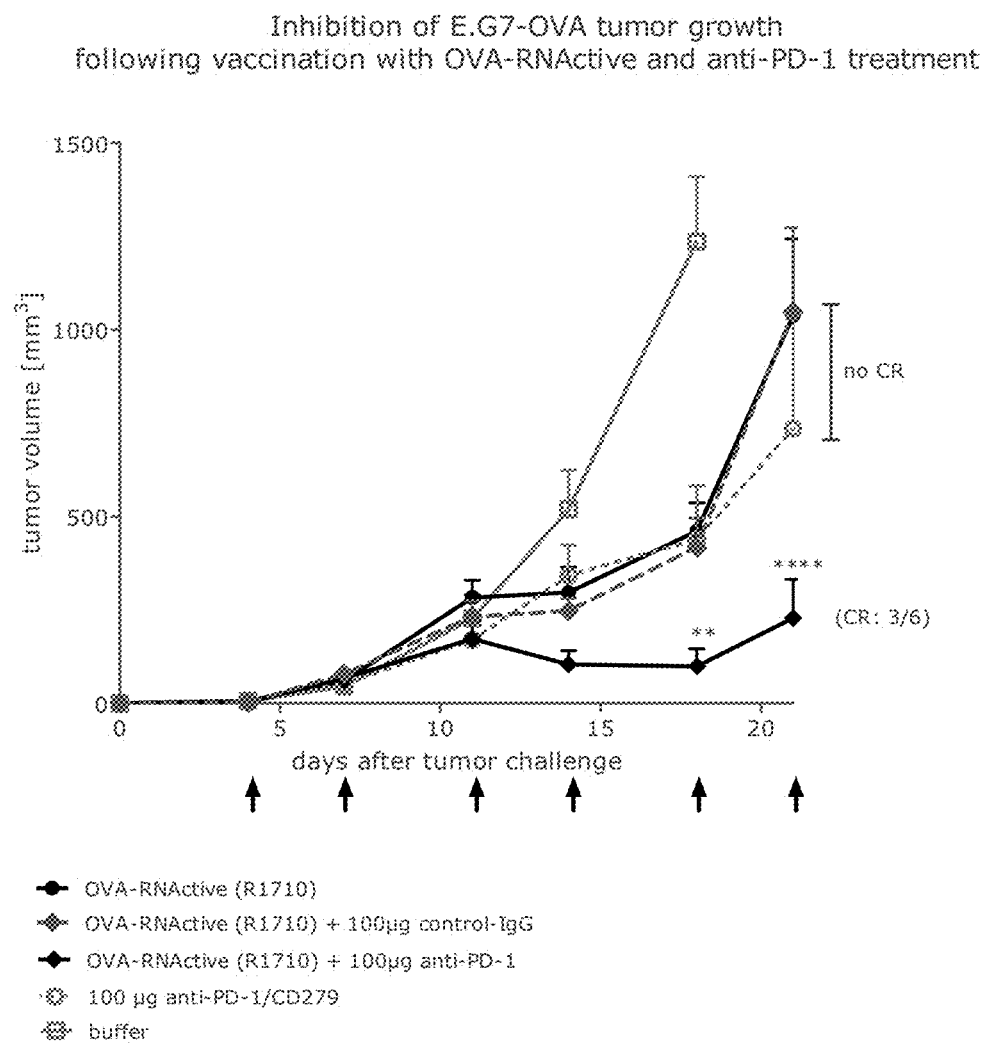
FIG. 1: The RNA vaccine (OVA-RNActive R1710) acts synergistically with anti-PD-1 antibody. C57 BL/6 mice were challenged subcutaneously with $3\times10^5$ syngenic E.G7-OVA tumor cells on day 0 and then treated with either OVA RNActive vaccine (32 µg) alone or in combination with anti-PD-1 antibody or control IgG (100 µg i.p.) in accordance with the indicated schedule.

The examples shown in the following are merely illustrative and shall describe the present invention in a further way. These examples shall not be construed to limit the present invention thereto.

Example 1: Preparation of the mRNA Vaccine

1. Preparation of DNA and mRNA Constructs
   For the present examples a DNA sequence, encoding *Gallus gallus* ovalbumin mRNA (R1710) was prepared and used for subsequent in vitro transcription reactions.
   According to a first preparation, the DNA sequence coding for the above mentioned mRNA was prepared. The construct was prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop. In SEQ ID NO: 2 (see FIG. 3) the sequence of the corresponding mRNA is shown.
2. In Vitro Transcription
   The respective DNA plasmid prepared according to Example 1 was transcribed in vitro using T7 polymerase. Subsequently the mRNA was purified using PureMessenger® (CureVac, Tubingen, Germany).
3. Reagents
   Complexation Reagent: protamine
4. Preparation of the Vaccine
   The mRNA R1710 was complexed with protamine by addition of protamine to the mRNA in the ratio (1:2) (w/w) (adjuvant component). After incubation for 10 min, the same amount of free mRNA R1710 used as antigen-providing RNA was added.
   OVA-RNActive vaccine (R1710): comprising an adjuvant component consisting of mRNA coding for *Gallus gallus* ovalbumin (R1710) according to SEQ ID NO. 2 complexed with protamine in a ratio of 2:1 (w/w) and the antigen-providing free mRNA coding for *Gallus*

*gallus* ovalbumin (R1710) according to SEQ ID NO. (ratio 1:1; complexed RNA:free RNA).

Example 2: Combination of an Anti-PD1 Antibody and an RNA Vaccine

On day zero, C57BL/6 mice were implanted subcutaneously (right flank) with 3×10⁵ E.G7-OVA cells per mouse (volume 100 μl in PBS). E.G7-OVA is a mouse T cell lymphoma cell line stably expressing *Gallus gallus* ovalbumin (OVA). Intradermal vaccination with the RNA vaccine comprising OVA mRNA R1720 (32 μg/mouse/vaccination day) (according to Example 1) or Ringer-lactate (RiLa) as buffer control and treatment with the anti-PD-1/CD279 monoclonal antibody (100 μg i.p.) or an isotype control according to Table 1 started on day 4 and was repeated on days 7, 11, 14, 18 and 21. Animals received the antibody injection in the morning and were vaccinated in the afternoon with a minimum of four hours between the treatments.

TABLE 1

Animal groups

| Group | Number of mice | Injected RNA per vaccination day and mouse | Injected antibody per treatment day and mouse |
|---|---|---|---|
| A | 10 | 100% Ringer Lactate (RiLa) buffer | — |
| B | 10 | 32 μg | — |
| C | 6 | — | 100 μg anti-PD-1 |
| D | 6 | 32 μg | 100 μg anti-PD-1 |
| E | 6 | 32 μg | 100 μg control-IgG2a |

The anti-PD-1/CD279 antibody (clone RMP1-14, rat IgG2a) and the isotype control antibody (clone 2A3, rat IgG2a) were purchased from BioXCell (West Lebanon, N.H., USA).

Tumour growth was monitored by measuring the tumour size in 2 dimensions (length and width) using a caliper (starting on day 4). Tumour volume was calculated according to the following formula:

$$\text{volume}(mm^3) = \frac{\text{length}(mm) \times \pi \times \text{width}^2(mm^2)}{6}$$

Figure 2:
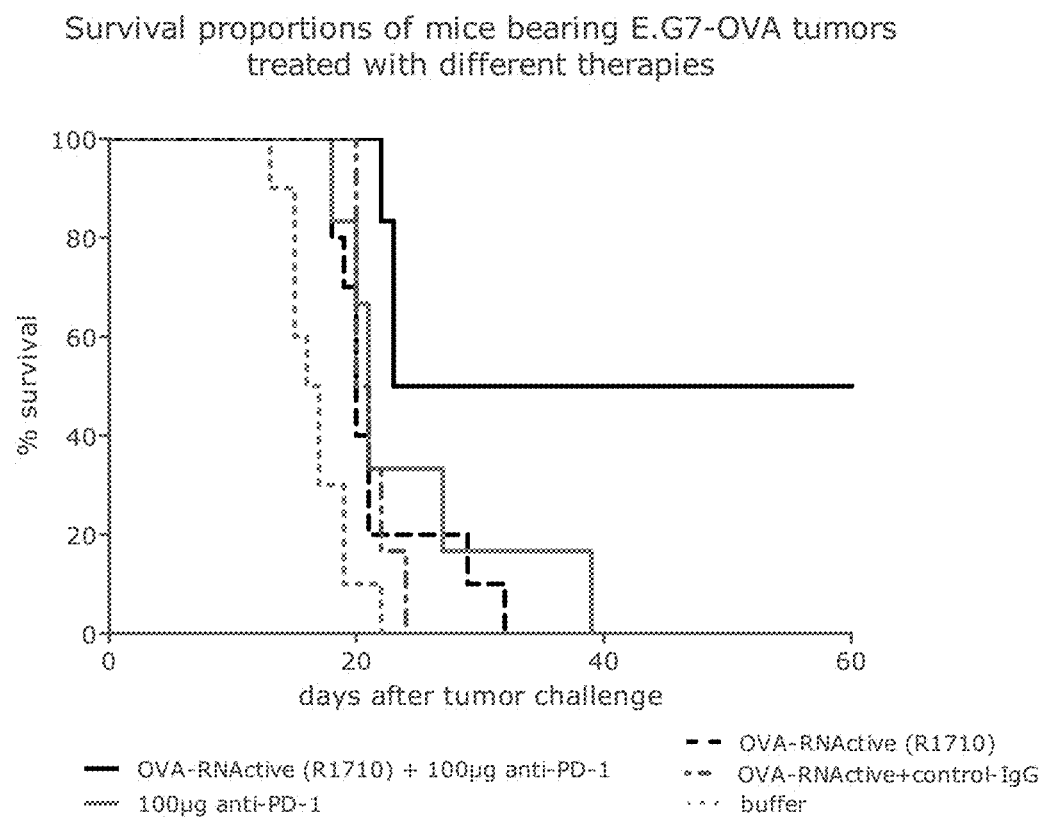
FIG. 2: Survival proportions of mice bearing E.G7-OVA tumors treated with different therapies. According to Example 2, mice were treated with either OVA-RNActive vaccine or anti-PD-1 antibody alone or in combination.

The results are shown in FIGS. 1 and 2.

As can be seen in FIG. 1, the OVA mRNA vaccine (OVA-RNActive R1710) alone or in combination with control-IgG delayed tumor growth by approximately 5 days compared to the buffer-treated control group. Treatment with anti-PD-1 antibody alone was comparable to vaccination alone, whereas simultaneous application of the RNA vaccine/anti-PD-1 combination led to significant inhibition of tumor growth, indicating a synergistic effect. Lines represent the development of mean tumor volume and error bars the SEM. Statistical analysis was based on the 2way Anova with Bonferroni posttest.

As can be seen in FIG. 2, the administration of the OVA mRNA vaccine (OVA-RNActive R1710) or anti-PD-1 antibody alone had already a significant effect on survival, whereas simultaneous application of the RNA vaccine/anti-PD-1 combination led to 50% survival (3 of 6 animals), indicating a synergistic effect.

The invention claimed is:

1. A method of treating a subject having a cancer or a tumor disease, the method comprising administering to the subject an effective amount of:
   (i) an immunogenic composition comprising at least one mRNA comprising at least one open reading frame (ORF) encoding at least one tumour-specific antigen (TSA), or an antigenic fragment of a TSA, wherein said mRNA comprises a 5' Cap and a Poly-A sequence of about 25 to about 400 adenosine nucleotides; and
   (ii) a PD-1 pathway inhibitor, said PD-1 pathway inhibitor comprising an antagonistic antibody directed against PD-1 or PD-L1.

2. The method of claim 1, wherein the tumour-specific antigen (TSA) consists of one antigenic one epitope.

3. The method of claim 1, wherein the tumour-specific antigen (TSA) comprises multiple antigenic epitopes.

4. The method of claim 1, wherein the tumour-specific antigen (TSA) results from a tumour specific mutation.

5. The method of claim 1, wherein the tumour-specific antigen (TSA) results from a tumour specific mutation in a tumor antigen selected from the group consisting of 5T4, 707-AP, 9D7, AFP, AlbZIP HPG1, alpha-5-beta-1-integrin, alpha-5-beta-6-integrin, alpha-actinin-4, alpha-methylacyl-coenzyme A racemase, ART-4, ARTC1, B7H4, BAGE-1, BCL-2, bcr/abl, beta-catenin, BING-4, BRCA1, BRCA2, CA 15-3/CA 27-29, CA 19-9, CA72-4, CA125, calreticulin, CAMEL, CASP-8, cathepsin B, cathepsin L, CD19, CD20, CD22, CD25, CDE30, CD33, CD4, CD52, CD55, CD56, CD80, CDC27, CDK4, CDKN2A, CEA, CLCA2, CML28, CML66, COA-1, coactosin-like protein, collage XXIII, COX-2, CT-9/BRD6, Cten, cyclin B1, cyclin D1, cyp-B, CYPB1, DAM-10, DAM-6, DEK-CAN, EFTUD2, EGFR, ELF2, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB, HAGE, HAST-2, hepsin, Her2/neu, HERV-K-MEL, HLA-A*0201-R17I, HLA-A11, HLA-A2, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2, matrix protein 22, MC1R, M-CSF, ME1, mesothelin, MG50/PXDN, MMP11, MN/CA IX-antigen, MRP-3, MUC-1, MUC-2, MUM-1, MUM-2, MUM-3, myosin class I, NA88-A, N-acetylglucosaminyl-transferase-V, Neo-PAP, Neo-PAP, NFYC, NGEP, NMP22, NPM/ALK, N-Ras, NSE, NY-ESO-B, NY-ESO-1, OA1, OFA-iLRP, OGT, OGT, OS-9, OS-9, osteocalcin, osteopon-tin, p15, p190 minor bcr-abl, p53, p53, PAGE-4, PAI-1, PAI-2, PAP, PART-1, PATE, PDEF, Pim-1-Kinase, Pin-1, Pml/PARalpha, POTE, PRAME, PRDX5, prostein, protei-nase-3, PSA, PSCA, PSGR, PSM, PSMA, PTPRK, RAGE-1, RBAF600, RHAMM/CD168, RU1, RU2, S-100, SAGE, SART-1, SART-2, SART-3, SCC, SIRT2, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI, TRAG-3, TRG, TRP-1, TRP-2/6b, TRP/INT2, TRP-p8, tyrosinase, UPA, VEGFR1, VEGFR-2/FLK-1, and WT1.

6. The method of claim 1, wherein the tumour-specific antigen (TSA) is selected from the group consisting of alpha-actinin-4, bcr/abl, beta-catenin, BRCA1, BRCA2, CASP-8, CDC27, CDK4, CDKN2A, COA-1, EFTUD2, ELF2, GPNMB, HLA-A*0201-R17I, HLA-A11, HLA-A2, KIAA0205, K-Ras, MART-2, ME1, MUM-1, MUM-2, MUM-3, myosin class I, Neo-PAP, NFYC, N-Ras, OGT, OS-9, p190 minor bcr-abl, p53, PRDX5, PTPRK, RBAF600, SIRT2, TPI.

7. The method of claim 1, wherein the at least one open reading frame is codon optimized for the human codon usage.

8. The method of claim 1, wherein the at least one open reading frame of the at least one mRNA comprises an increased G/C content relative to the open reading frame of a wild type mRNA encoding the tumour-specific antigen (TSA).

9. The method of claim 1, wherein the at least one mRNA is chemically modified.

10. The method of claim 1, wherein the at least one open reading frame (ORF) encodes at least two different epitopes of at least two different tumour-specific antigens (TSA).

11. The method of claim 1, wherein the immunogenic composition comprises at least two different mRNAs each comprising at least one open reading frame (ORF) encoding different tumour-specific antigens (TSA).

12. The method of claim 1, wherein the at least one mRNA is complexed with a carrier.

13. The method of claim 12, wherein the carrier is a cationic, polycationic or polymeric carrier.

14. The method of claim 12, wherein the carrier comprises protamine.

15. The method of claim 12, wherein the carrier comprises a cationic or polycationic lipid.

16. The method of claim 1, wherein the PD-1 pathway inhibitor is administered after said immunogenic composition.

17. The method of claim 1, wherein the immunogenic composition and the PD-1 pathway inhibitor are administered sequentially.

18. The method of claim 1, wherein the immunogenic composition and the PD-1 pathway inhibitor are administered concurrently.

19. The method of claim 1, wherein the immunogenic composition and the PD-1 pathway inhibitor are administered via different administration routes.

20. The method of claim 11, wherein said two different RNAs encode:

i) NY-ESO-1, or an antigenic fragment thereof; and ii) MAGE-A3, or an antigenic fragment thereof.

21. The method of claim 20, wherein said two different RNAs encode:

i) NY-ESO-1; and ii) MAGE-A3.

22. The method of claim 20, wherein the immunogenic composition further comprises a mRNA encoding tyrosinase, or an antigenic fragment thereof.

23. The method of claim 20, wherein the PD-1 pathway inhibitor is an anti-PD1 antibody.

24. The method of claim 23, wherein the subject has a melanoma.

25. The method of claim 24, wherein the immunogenic composition is administered by intravenous injection.

* * * * *

UNITED STATES PATENT AND TRADEMARK OFFICE
CERTIFICATE OF CORRECTION

PATENT NO. : 11,458,195 B2
APPLICATION NO. : 16/555586
DATED : October 4, 2022
INVENTOR(S) : Mariola Fotin-Mleczek, Karl-Josef Kallen and Jochen Probst Page 1 of 1

It is certified that error appears in the above-identified patent and that said Letters Patent is hereby corrected as shown below:

On the Title Page

Item (30) insert:
--(30) Foreign Application Priority Data
Feb. 22, 2013 (WO) . . . . . . . PCT/EP2013/000526--.

Signed and Sealed this
Fourth Day of April, 2023

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 44
<212> TYPE: DNA
<213> ORGANISM: Artificial Sequence
<220> FEATURE:
<223> OTHER INFORMATION: muag (mutated (alpha-) globin 3' UTR)

<400> SEQUENCE: 1
gcccgatggg cctcccaacg ggccctcctc ccctccttgc accg                44

<210> SEQ ID NO 2
<211> LENGTH: 1378
<212> TYPE: RNA
<213> ORGANISM: Artificial Sequence
<220> FEATURE:
<223> OTHER INFORMATION: mRNA corresponding to artificial DNA construct

<400> SEQUENCE: 2
gggagaaagc uuaccauggg cagcaucggg gccgcgucga uggaguucug cuucgacgug      60
uucaaggagc ugaaggucca ccacgccaac gagaacaucu ucuacugccc gaucgccauc     120
augagcgcgc ucgccauggu guaccugggc gccaaggaca gcacccggac gcagaucaac     180 aaggugucc gcuucgacaa gcugcccggc uucggggacu cgaucgaggc gcagugcggc     240
accagcguga acgugcacag cucgcuccgg gacauccuga accagaucac caagccgaac     300
gacgucuaca gcuucagccu ggccucgcgg cucuacgccg aggagcgcua cccgauccug     360
cccgaguacc ugcagugcgu gaaggagcuc uaccggggcg ggcuggagcc gaucaacuuc     420

```
cagacggcgg ccgaccaggc ccgggagcug aucaacagcu ggguggagag ccagaccaac    480
ggcaucaucc gcaacguccu ccagccgucg agcguggaca gccagaccgc gauggugcug    540
gucaacgcca ucguguucaa gggccugugg gagaagacgu caaggacga ggacacccag     600 gccaugcccu uccggguga cgagcaggag ucgaagccgg uccagaugau guaccagauc     660
gggcucuucc ggguggcgag cauggccagc gagaagauga agauccugga gcugccguuc    720
gccucgggca cgaugagcau gcucgugcug cugcccgacg aggucagcgg ccucgagcag    780
cuggagucga ucaucaacuu cgagaagcug accgaguga ccagcagcaa cgugauggag     840
gagcgcaaga ucaaggugua cucccgcgcg augaagaugg aggagaagua caaccugacg    900
ucgguccuga uggcgauggg gaucaccgac guguucagca gcucggccaa ccucagcggc    960
aucagcucgg ccgagagccu gaagaucagc caggcggugc acgccgccca cgcggagauc   1020
aacgaggccg ccgggaggu cguggggucg gccgaggcgg gcguggacgc cgccagcguc   1080
agcgaggagu ccgcgcgga ccacccguuc cuguucugca ucaagcacau cgccaccaac    1140
gccgugcucu ucuucggccg gugcgugucg cccugaccac uaguuauaag acugacuagc   1200
ccgaugggcc ucccaacggg ccccuccuccc cuccuugcac cgagauuaau aaaaaaaaaa   1260
aaaaaaaaaa aaaaaaaaaa aaaaaaaaaa aaaaaaaaaa aaaaaaaaaa aaaaugcauc   1320
cccccccccc cccccccccc cccccccccc aaaggcucuu uucagagcca ccagaauu     1378

<210> SEQ ID NO 3
<211> LENGTH: 7
<212> TYPE: PRT
<213> ORGANISM: Artificial Sequence
<220> FEATURE:
<223> OTHER INFORMATION: cationic peptide

<400> SEQUENCE: 3

Arg Arg Arg Arg Arg Arg Arg
1               5

<210> SEQ ID NO 4
<211> LENGTH: 8
<212> TYPE: PRT
<213> ORGANISM: Artificial Sequence
<220> FEATURE:
<223> OTHER INFORMATION: cationic peptide

<400> SEQUENCE: 4

Arg Arg Arg Arg Arg Arg Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: cationic peptide

<400> SEQUENCE: 5

Arg Arg Arg Arg Arg Arg Arg Arg Arg
1               5

<210> SEQ ID NO 6
<211> LENGTH: 12
<212> TYPE: PRT
<213> ORGANISM: Artificial Sequence
<220> FEATURE:
<223> OTHER INFORMATION: cationic peptide
```

```
<400> SEQUENCE: 6

His His His Arg Arg Arg Arg Arg Arg Arg Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: cationic peptide

<400> SEQUENCE: 7

Arg Arg Arg Arg Arg Arg Arg Arg Arg His His His
1               5                   10

<210> SEQ ID NO 8
<211> LENGTH: 15
<212> TYPE: PRT
<213> ORGANISM: Artificial Sequence
<220> FEATURE:
<223> OTHER INFORMATION: cationic peptide

<400> SEQUENCE: 8

His His His Arg Arg Arg Arg Arg Arg Arg Arg Arg His His His
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: cationic peptide

<400> SEQUENCE: 9

Tyr Ser Ser Arg Arg Arg Arg Arg Arg Arg Arg Arg Ser Ser Tyr
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: cationic peptide

<400> SEQUENCE: 10

Arg Lys His Arg Lys His Arg Lys His Arg Lys His
1               5                   10

<210> SEQ ID NO 11
<211> LENGTH: 8
<212> TYPE: PRT
<213> ORGANISM: Artificial Sequence
<220> FEATURE:
<223> OTHER INFORMATION: cationic peptide

<400> SEQUENCE: 11

Tyr Arg Lys His Arg Lys His Arg
1               5

<210> SEQ ID NO 12
<211> LENGTH: 12
<212> TYPE: PRT
<213> ORGANISM: Artificial Sequence
<220> FEATURE:
<223> OTHER INFORMATION: cationic peptide
```

```
<400> SEQUENCE: 12

Arg Arg Arg Arg Arg Arg Arg Arg Arg Arg Arg
1               5                   10

<210> SEQ ID NO 13
<211> LENGTH: 21
<212> TYPE: PRT
<213> ORGANISM: Artificial Sequence
<220> FEATURE:
<223> OTHER INFORMATION: cationic peptide

<400> SEQUENCE: 13

His His His His His His Arg Arg Arg Arg Arg Arg Arg Arg Arg His
1               5                   10                  15

His His His His His
            20

<210> SEQ ID NO 14
<211> LENGTH: 10
<212> TYPE: PRT
<213> ORGANISM: Artificial Sequence
<220> FEATURE:
<223> OTHER INFORMATION: cationic peptide

<400> SEQUENCE: 14

His His His Arg Arg Arg Arg His His His
1               5                   10

<210> SEQ ID NO 15
<211> LENGTH: 16
<212> TYPE: PRT
<213> ORGANISM: Artificial Sequence
<220> FEATURE:
<223> OTHER INFORMATION: cationic peptide

<400> SEQUENCE: 15

His His His His His His Arg Arg Arg Arg His His His His His His
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: cationic peptide

<400> SEQUENCE: 16

Tyr Ser Ser Arg Arg Arg Arg Arg Arg Arg Arg Ser Ser Tyr
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: cationic peptide

<400> SEQUENCE: 17

Arg Lys His Arg Lys His Arg Lys His Arg Lys His
1               5                   10

<210> SEQ ID NO 18
<211> LENGTH: 8
<212> TYPE: PRT
<213> ORGANISM: Artificial Sequence
<220> FEATURE:
```

<223> OTHER INFORMATION: cationic peptide

<400> SEQUENCE: 18

Tyr Arg Lys His Arg Lys His Arg
1               5